(12) United States Patent
Castro et al.

(10) Patent No.: US 7,745,464 B2
(45) Date of Patent: Jun. 29, 2010

(54) COMPOUNDS AND METHODS FOR INHIBITING THE INTERACTION OF BCL PROTEINS WITH BINDING PARTNERS

(76) Inventors: Alfredo C. Castro, 43 Wildwood St., Winchester, MA (US) 01890; Michael J. Grogan, 36 Academy St., Arlington, MA (US) 02476; Edward B. Holson, 66 Forest St., Newton Highlands, MA (US) 02461; Brian T. Hopkins, 1454 Beacon St., #341, Brookline, MA (US) 02446; Nii O. Koney, 276 Chestnut Hill Ave., #2, Brighton, MA (US) 02135; Stephane Peluso, 97 Josephine Ave., Somerville, MA (US) 02144; Daniel A. Snyder, 109 Windsor St., #5, Cambridge, MA (US) 02139

( * ) Notice: Subject to any disclaimer, the term of this patent is extended or adjusted under 35 U.S.C. 154(b) by 526 days.

(21) Appl. No.: 11/640,480

(22) Filed: Dec. 15, 2006

(65) Prior Publication Data

US 2007/0155705 A1      Jul. 5, 2007

Related U.S. Application Data

(60) Provisional application No. 60/750,987, filed on Dec. 16, 2005.

(51) Int. Cl.
*A61K 31/445* (2006.01)
*C07D 295/00* (2006.01)

(52) U.S. Cl. ................ 514/315; 514/365; 514/423; 548/530; 548/200; 546/245

(58) Field of Classification Search ............... 548/530, 548/200; 546/245; 514/315, 365, 423
See application file for complete search history.

(56) References Cited

U.S. PATENT DOCUMENTS

| 6,747,050 | B1 | 6/2004 | Kim et al. |
| 2004/0147473 | A1 | 7/2004 | Warrell |
| 2005/0032714 | A1 | 2/2005 | Warrell |
| 2006/0025460 | A1 | 2/2006 | Castro et al. |
| 2006/0199817 | A1* | 9/2006 | Tasker et al. ............. 514/234.5 |
| 2008/0293731 | A1 | 11/2008 | Feuerbach et al. |
| 2009/0133319 | A1 | 5/2009 | Lahm et al. |

FOREIGN PATENT DOCUMENTS

| EP | 0 970 950 | 1/2000 |
| WO | WO 02/17852 | 3/2002 |
| WO | WO 02/097053 | 12/2002 |
| WO | WO 03/015788 | 2/2003 |
| WO | WO 2006/009869 | 1/2006 |
| WO | WO 2007/068476 | 6/2007 |
| WO | WO 2007/075459 | 7/2007 |

OTHER PUBLICATIONS

Kuramochi et al., 2004, CAS: 142: 74358.*
Tanaka et al., 1991, CAS: 114: 81225.*
Carboni et al. CAS: 141:360665.*
Tasker et al., 2006, CAS: 145: 315004.*
Dong et al., 2005, CAS: 143:153230.*
Pulley, H. et al., "Small-molecule inhibitors of Bcl-2 protein", *Drugs Fut.*, 29(4):369-381 (Prous Science)(2004).
International Search Report dated Jun. 12, 2007.
Baell, J.B., et al. "Prospects for Targeting the BCL-2 Family of Proteins to Develop Novel Cytotoxic Drugs." *Biochemical Pharmacology* 64: 851-863 (2002).
Ding, X. et al. "Catalytic Asymmetric 1,3-Dipolar Cycloaddition of a Nitrone Bearing a Bulky Amide Moiety to gamma-Substituted Allylic Alcohols." *Chemistry Letters* 2002: 302-303 (2002).
Akmanova, N. A. et al. "Dipolar Addition to Carbamoyl Nitrones." *Journal of Organic Chemistry of the USSR* 15(10):1863-1866 (1979).
Ratts, K. W. et al. "Chemistry of Resonance Stabilized Sulfonium Ylids." *Journal of Organic Chemistry* 31(6): 1689-1693 (1966).
Oltersdorf, T. et al. "An Inhibition of BCL-2 Family Proteins Induces Regression of Solid Tumors." *Nature* 435: 677-681 (2005).

* cited by examiner

*Primary Examiner*—Rei-tsang Shiao
(74) *Attorney, Agent, or Firm*—Foley Hoag LLP

(57) ABSTRACT

The present invention relates to heterocyclic compounds that bind to Bcl proteins and inhibit Bcl function, compositions comprising such compounds, and methods for treating and modulating disorders associated with hyperproliferation, such as cancer.

18 Claims, No Drawings

COMPOUNDS AND METHODS FOR INHIBITING THE INTERACTION OF BCL PROTEINS WITH BINDING PARTNERS

RELATED APPLICATIONS

This application claims the benefit of U.S. Provisional Patent Application Ser. No. 60/750,987, filed Dec. 16, 2005.

BACKGROUND OF THE INVENTION

The present invention generally relates to heterocyclic compounds useful for treating cancer.

Apoptosis, or programmed cell death, is important for normal embryological/anatomical development, host defense and suppression of oncogenesis. Faulty regulation of apoptosis has been implicated in cancer and in many other human diseases which result from an imbalance between the process of cell division and cell death. A central check point of apoptosis is the regulation of cytochrome c release from mitochondria. Cytochrome c release is regulated, in part, by Bcl-2 family members. The Bcl-2 family of proteins includes both anti-apoptotic molecules, such as Bcl-2 and Bcl-XL, and pro-apoptotic molecules, such as Bax, Bak, Bid and Bad. Bcl-2 contributes to cancer cell progression by preventing normal cell turnover caused by physiological cell-death mechanisms. Over-expression of Bcl-2 has been observed in 70% of breast cancer and many other forms of cancer.

Various small molecules have been shown to inhibit the function of Bcl-2. Nevertheless, the need exists for additional small organic molecules that bind to Bcl-2 and block its anti-apoptotic function in cancer and promote cell death in tumors.

SUMMARY OF THE INVENTION

One aspect of the invention relates to heterocyclic compounds and pharmaceutically acceptable salts of these compounds. In certain instances, the heterocyclic compound comprises a nitrogen containing five membered heterocyclic core, such as a pyrrolidine, oxazolidine, thiazolidine, imidazolidine, or pyrazolidine, and unstaturated derivatives thereof. In other instances, the heterocyclic compound comprises a nitrogen containing six membered heteocyclic core, such as a piperidine, morpholine, piperazine, thiopiperazine, and unsaturated derivatives thereof. In certain instances, the five or six membered heterocylic ring may be susbstitued with an oxo or thioxo group (e.g., pyrrolidone, oxazolidinone, imidazolidone, thiazolidone); a nitrogen atom of the heterocyclic ring is bonded to a substituted aralkyl group; the substituted aralkyl group is a substituted benzyl group; the heterocyclic ring is substituted with a hydroxy methyl or hydroxy ethyl group; the heterocyclic ring is substituted with a hydroxy methyl and a hydroxy ethyl group; and/or the heterocyclic ring is substituted with an amide group.

Another aspect of the invention relates to pharmaceutical compositions comprising one or more of the heterocyclic compounds of the invention, or salts thereof. A further aspect of the present invention relates to a method of using the above compounds, or pharmaceutically acceptable salts thereof, alone or in combination with other agents to treat cancer.

Specifically, the invention provides a therapeutic method comprising treating a condition characterized by the pathological proliferation of mammalian cells by administering an effective amount of a compound of the present invention.

DETAILED DESCRIPTION OF THE INVENTION

Definitions

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

As used herein, the definition of each expression, e.g., alkyl, m, n, etc., when it occurs more than once in any structure, is intended to be independent of its definition elsewhere in the same structure.

The term "acylamino" refers to a moiety that may be represented by the general formula:

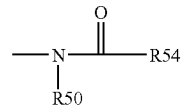

wherein R50 is as defined below, and R54 represents a hydrogen, an alkyl, an alkenyl or —$(CH_2)_m$—R61, where m and R61 are as defined below.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" refers to an alkyl group, as defined above, having an oxygen radical attached thereto. Representative alkoxyl groups include methoxy, ethoxy, propyloxy, tert-butoxy and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., C1-C30 for straight chain, C3-C30 for branched chain), and in other embodiments 20 or fewer. Likewise, in certain embodiments cycloalkyls have from 3-10 carbon atoms in their ring structure, and in other embodiments have 5, 6 or 7 carbons in the ring structure. In certain embodiments cycloalkyls, bicycloalkyls, and polycylcloalkyls can be further substituted with one or more alkyl subsituents.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined below. Representative alkylthio groups include methylthio, ethyl thio, and the like.

The term "amido" is art recognized as an amino-substituted carbonyl and includes a moiety that may be represented by the general formula:

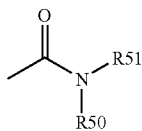

wherein R50 and R51 are as defined below. Certain embodiments of the amide in the present invention will not include imides which may be unstable.

The terms "amine" and "amino" are art-recognized and refer to both unsubstituted and substituted amines, e.g., a moiety that may be represented by the general formulas:

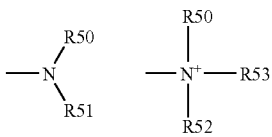

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "aralkyl", as used herein, refers to an alkyl group substituted with an aryl group (e.g., an aromatic or heteroaromatic group).

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "carboxyl" is includes such moieties as may be represented by the general formulas:

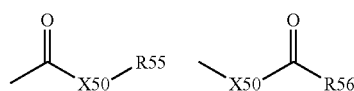

wherein X50 is a bond or represents an oxygen or a sulfur, and each of R55 and R56 represents independently a hydrogen, an alkyl, an alkenyl, —(CH$_2$)$_m$—R61 or a pharmaceutically acceptable salt, where m and R61 are defined above.

The term "diradical" or "bivalent" as used herein are used interchangeably and refer to any of a series of divalent groups from alkyl, alkenyl, alkynyl, alkylamino, alkoxyl, cycloalkyl, heterocycloalkyl, aryl, aralkyl, heterocyclyl, heteroaryl, and heteroaralkyl groups. For example,

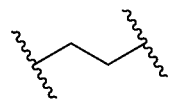

is a bivalent alkyl or alkyl diradical;

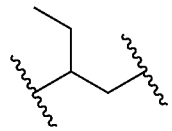

is also a bivalent alkyl or alkyl diradical;

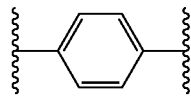

is a bivalent aryl or aryl diradical;

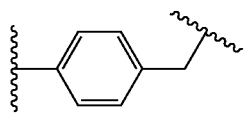

is a bivalent aralkyl or aralkyl diradical; and

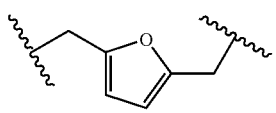

is a bivalent (alkyl)heteroaralkyl or (alkyl)heteroaralkyl diradical. Typical examples include alkylenes of general structure (CH$_2$)$_X$ where X is 1-6, and corresponding alkenylene and alkynylene linkers having 2-6 carbon atoms and one or more double or triple bonds; cycloalkylene groups having 3-8 ring members; and aralkyl groups wherein one open valence is on the aryl ring and one is on the alkyl portion such as

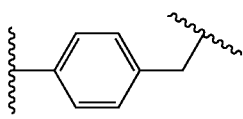

and its isomers.

The term "haloalkyl", as used herein, refers to an alkyl group where anywhere from 1 to all hydgrogens have been replaced with a halide. A "perhaloalkyl" is where all of the hydrogens have been replaced with a halide.

The term "heteroatom" as used herein means an atom of any element other than carbon or hydrogen. Examples of heteroatoms include boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

As used herein, the term "nitro" means —NO2; the term "halogen" designates —F, —Cl, —Br or —I; the term "sulfhydryl" means —SH; the term "hydroxyl" means —OH; and the term "sulfonyl" means —SO2—.

The term "oxo" refers to a carbonyl oxygen (═O).

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The terms "triflyl", "tosyl", "mesyl", and "nonaflyl" refer to trifluoromethanesulfonyl, p-toluenesulfonyl, methanesulfonyl, and nonafluorobutanesulfonyl groups, respectively. The terms "triflate", "tosylate", "mesylate", and "nonaflate" to trifluoromethanesulfonate ester, p-toluenesulfonate ester, methanesulfonate ester, and nonafluorobutanesulfonate ester functional groups and molecules that contain said groups, respectively.

The term "thioxo" refers to a carbonyl sulfur (═S).

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Certain compounds may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The phrases "Bcl-mediated disorder" and "disorder mediated by cells expressing Bcl proteins" refer to pathological and disease conditions in which a Bcl protein plays a role. Such roles may be directly related to the pathological condition or may be indirectly related to the condition. The feature common to this class of conditions is that they may be ameliorated by inhibiting the activity of, function of, or association with Bcl proteins.

As used herein, the terms "Bcl" and "Bcl protein" are intended to encompass one or more of the Bcl-2 subfamily of anti-apoptotic proteins Bcl-2, Bcl-w, Mcl-1, Bcl-XL, A1, Bfl1, Bcl-B, BOO/DIVA, and their homologues.

Synthesis of Heterocyclic Compounds

In certain instances, the heterocyclic compounds of the present invention are five membered heterocycles. The five membered heterocycles can be prepared from the reaction of triphosgene, thiophosgene, thionylchloride, sulfonylchloride and the like, and 1,2 amino alcohols, 1,2 amino thiols, or 1,2 diamines. In certain instances, the five membered heterocycles of the present invention can be prepared by the reaction of an 1,2 amino alcohol, 1,2 amino thiol, or 1,2 diamine with an aldehyde or ketone. In certain instances, the heterocycles of the present invention can be synthesized from cyclizations of gamma amino acids to afford 2-pyrridones. In certain instances, the five membered heterocycles of the present invention can be synthesized using a [3+2] cycloaddition reaction between an azaallyl anion or azomethine ylide and an alkene. The azomethine ylide substrate and alkene may contain functional groups suitable for chemical derivatization following synthesis of a pyrrolidine core. In certain instances, a Lewis acid, e.g., AgOAc, is added to the reaction. In certain instances, the reaction mixture is subjected to heat. In general, the subject reactions are carried out in a liquid reaction medium, but can be carried out on a solid support. In certain instances, the heterocycles can be synthesized from the [3+2] cycloaddition of nitrones and allylic alcohols. The 5-methyl alcohol on the resulting cycloadducts can then be reacted with mesyl chloride to yield a 5-methyl-mesylate-isoxazolidine. Upon exposure to SmI, the N—O bond of the isoxazolidine is reduced and the amine spontaneously cyclizes to form a pyrrolidine, as described in the examples below (see also, U.S. Ser. No. 11/156,364, filed Jun. 17, 2005, Publication No. 20060025460, herein incorporated by reference in its entirety). Typically, the N—O bond reduction takes place in a protic solvent, such as methanol.

In certain embodiments, the heterocyclic compounds of the present invention are six membered heterocycles. These compounds can be made using a number of methods in the art. For example, the heterocycles can be synthesized using annulation strategies from acyclic precursors containing two nucleophilic species separated by three carbons. For example, 1,3 diamines, 1,3 amino alcohols, 1,3 diols, 1,3 dithions, 1,3 amino thiols, or 1,3 thiol alcohols can be cyclized using sulfonyl chloride, phosgene, or thiophosgene to generate a 6 membered ring. Likewise, six membered rings can be made by intermolecular or intramolecular condensation reactions, or [4+2] cycloaddition reactions. In addition, a number of six membered heterocycles are commercially available and can be modified to yield the compounds of the present invention.

Following synthesis of the heterocyclic core, the heterocyclic compounds may be derivatized using a variety of functionalization reactions known in the art. Representative examples include palladium coupling reactions to alkenylhalides or aryl halides, oxidations, reductions, reactions with nucleophiles, reactions with electrophiles, pericyclic reactions, installation of protecting groups, removal of protecting groups, and the like.

The heterocyclic compounds of the invention bind to one or more Bcl proteins and block Bcl anti-apoptotic function in cancer cells and tumor tissue that express the Bcl protein. In certain embodiments, compounds of the invention selectively inhibit the anti-apoptotic activity of only one member of the Bcl-2 subfamily of anti-apoptotic proteins. The heterocyclic compounds of the invention can be used to treat a patient suffering from a disease related to Bcl. In certain instances, the heterocyclic compounds of the invention are used to treat a patient suffering from cancer.

Biological Activity Analysis

The following in vitro binding and cellular assays can be used to determine the activity and specificity of compounds of the present invention to bind to Bcl-2 and inhibit Bcl-2 function in a cell.

Bcl-2 Binding Assay

Bcl-2 and Bcl-xL binding can be determined using a variety of known methods. One such assay is a sensitive and quantitative in vitro binding assay using fluorescence polarization (FP) described by Wang, J.-L.; Zhang, Z-J.; Choksi, S.; Sjam. S.; Lu, Z.; Croce, C. M.; Alnemri, E. S.; Komgold, R.; Huang, Z. Cell permeable Bcl-2 binding peptides: a chemical approach to apoptosis induction in tumor cells. Cancer Res. 2000, 60, 1498-1502).

Cell Based Assays

The ability of heterocyclic compounds of the present invention to inhibit cell-viability in cancer cells with Bcl-2 protein over-expression was demonstrated. When RL-cells are exposed to the heterocyclic compounds of the present invention, the inhibitors show a dose-dependent cell-killing in the Alamar blue cytoxicity assay with $IC_{50}$ values of from about 100 µM to about 1 µM (See Examples). When Panc1 cells are exposed to the heterocyclic compounds of the present invention in combination with camptothecin, the inhibitors show a synergistic dose-dependent cell killing in the propidium iodide exclusion cell survival assay with $IC_{50}$ values of from about 100 µM to about 1 µM (See Examples).

Bcl-2 inhibitors have been shown to be active against a number of cancer cell lines as single agent, including, but not limited to, breast cancer (US 2003/0119894, published PCT applications WO 02/097053 and WO 02/13833; all of which are hereby incorporated by reference), lymphomas (Nature (2005) 435, 677-681), small cell lung cancer (Nature (2005) 435, 677-681), head and neck cancer (published PCT application WO 02/097053; hereby incorporated by reference), and leukemias (published PCT application WO 02/13833; hereby incorporated by reference).

Bcl-2 inhibitors have been shown to be active against a number of cancer cell lines in combination with other anticancer agents and radiation, including, but not limited to, breast cancer (With docetaxel, published PCT application WO 02/097053; hereby incorporated by reference), prostate cancer (With docetaxel, published PCT application WO 02/097053; hereby incorporated by reference), head and neck cancer (With docetaxel, published PCT application WO 02/097053; hereby incorporated by reference), and non small-cell lung cancer (With paclitaxel, Nature (2005) 435, 677-681). In addition to the aforementioned combination chemotherapeutics, small molecule inhibitors of Bcl-2 proteins display synergy with other anticancer agents, including, but not limited to etoposide, doxorubicin, cisplatin, paclitaxel, and radiation (Nature (2005) 435, 677-681).

Methods of Therapy and Treatment

The present invention further provides methods for treating and reducing the severity of cancer as well as other Bcl-mediated disorders or conditions.

Cancers or neoplastic diseases and related disorders that can be treated by administration of compounds and compositions of the present invention, include, but are not limited to those listed below (for a review of such disorders, see Fishman et al., 1985, Medicine, 2d Ed., J. B. Lippincott Co., Philadelphia): Leukemia (including acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, and chronic lymphocytic leukemia); Polycythemia vera; Lymphoma (including Hodgkin's disease and non-Hodgkin's disease); Multiple myeloma; Waldenstrom's macroglobulinemia; Heavy chain disease; and Solid tumors (including fibrosarcoma, myxosarcoma, liposarcoma, chondrosarcoma, osteogenic sarcoma, chordoma, angiosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma).

In a preferred embodiment, the compounds of the present invention are used to treat cancers including, but not limited to, lymphomas (preferably follicular lymphoma, diffuse large B-cell lymphoma, mantle cell lymphoma, or chronic lymphocytic leukemia), prostrate cancer (more preferably hormone insensitive), breast cancer (preferably estrogen receptor positive), neuroblastoma, colorectal, endometrial, ovarian, lung (preferably small cell), hepatocellular carcinoma, multiple myeloma, head and neck or testicular cancer (preferably germ cell).

Treatment of Cancer in Combination with Chemotherapy or Radiotherapy

One or more compounds of the present invention can also be used to treat or prevent cancer or neoplastic disease in combination with one or more anti-cancer, chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, vinorelbine, paclitaxel, docetaxel, 5-FU, epipodophyllotoxin, camptothecin, 17-AAG, or cyclophosphamide. In a preferred embodiment, one or more compound of the present invention is used to treat or prevent cancer or neoplastic disease in combination with one or more chemotherapeutic or other anti-cancer agents including, but not limited to those shown below:

Radiation, e.g., γ-radiation; Nitrogen mustards (including cyclophosphamide, Ifosfamide, trofosfamide, Chlorambucil, Estramustine, and melphalan); Nitrosoureas (including carmustine (BCNU) and Lomustine (CCNU)); Alkylsulphonates (including busulfan and Treosulfan); Triazenes, such as Dacarbazine; Platinum containing compounds (including Cisplatin, carboplatin, and oxaplatin); Plant Alkaloids (including vincristine, Vinblastine, Vindesine, Vinorelbine, paclitaxel, and Docetaxol); DNA Topoisomerase Inhibitors (including etoposide, Teniposide, Topotecan, 9-aminocamptothecin, campto irinotecan, and crisnatol); mytomycin C; Anti-metabolites; Anti-folates (including methotrexate, Trimetrexate, mycophenolic acid, Tiazofurin, Ribavirin, EICAR, hydroxyurea, deferoxamine); Pyrimidine analogs (including 5-Fluorouracil, Floxuridine, Doxifluridine, Ratitrexed, capecitabine, cytarabine (ara C), Cytosine arabinoside, and fludarabine); Purine analogs (including mercaptopurine and Thioguanine); Hormonal therapies; Receptor antagonists (including Tamoxifen, Raloxifene, megestrol, goscrclin, Leuprolide acetate, flutamide, and bicalutamide); Retinoids/Deltoids (including EB 1089, CB1093, KH 1060, vertoporfin (BPD-MA), Phthalocyanine, photosensitizer Pc4, Demethoxy-hypocrellin A, (2BA-2-DMHA), Interferon α, Interferon γ, Tumor necrosis factor); and others (including Lovastatin, 1-methyl-4-phenylpyridinium ion, staurosporine, Actinomycin D, Dactinomycin, bleomycin A2, Bleomycin B2, Peplomycin, daunorubicin, Doxorubicin (adriamycin), Idarubicin, Epirubicin, Pirarubicin, Zorubicin, Mitoxantrone, verapamil, thapsigargin, Avastin, Erbitux, Rituxan, Prednisilone, Imatinib, Thalidomide, Lenalidomide, Bortezomib, Gemcitabine, Erlotinib, Gefitinib, Sorafenib, and Sutinib).

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

The heterocyclic compounds of the invention can be administered to a patient in the form of a pharmaceutical composition. The pharmaceutical composition comprises one or more of the heterocyclic compounds of the invention and one or more pharmaceutically acceptable excipients. In certain instances, the pharmaceutical composition comprises one or more heterocyclic compounds of the invention, one or more chemotherapeutic agents, and one or more pharmaceutically acceptable excipients.

In general, compounds of the present invention and the chemotherapeutic agent do not have to be administered in the same pharmaceutical composition, and may, because of different physical and chemical characteristics, have to be administered by different routes. For example, compounds of the present invention may be administered intravenously to generate and maintain good blood levels, while the chemotherapeutic agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemotherapeutic agent or radiation will depend upon the diagnosis of the attending physicians and their judgment of the condition of the patient and the appropriate treatment protocol.

A compound of the present invention, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with a compound of the present invention.

If a compound of the present invention, and the chemotherapeutic agent and/or radiation are not administered simultaneously or essentially simultaneously, then the optimum order of administration of the compound of the present invention, and the chemotherapeutic agent and/or radiation, may be different for different tumors. Thus, in certain situations the compound of the present invention may be administered first followed by the administration of the chemotherapeutic agent and/or radiation; and in other situations the chemotherapeutic agent and/or radiation may be administered first followed by the administration of a compound of the present invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of the present invention followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent, i.e., compound of the present invention, chemotherapeutic agent or radiation) of the treatment according to the individual patient's needs, as the treatment proceeds.

Compounds of the Invention

One aspect of the present invention relates to a compound represented by formula 1:

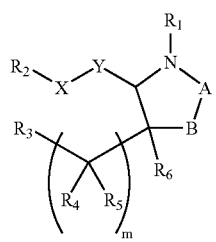

1 or an unsaturated form thereof or a pharmaceutically acceptable salt thereof;

wherein
Y is $-C(R_{10})_2-$, $-(C=O)-$, $-(C=S)-$, or $-C(=NR_{10})-$;
X is $-N(R_{10})-$, or a bond;
m is 0, 1, 2, 3, 4, 5, or 6;
A is $-S(O)-$, $-S(O)_2-$,

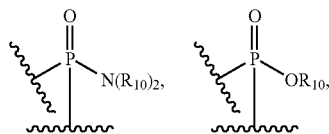

or $-C(A_1)(A_2)-$;

each of $A_1$ and $A_2$ is independently H, alkyl, alkenyl, alkynyl, aryl, cycloalkyl, aralkyl, heterocyclyl, heteroaryl, heteroaralkyl, $-C(O)N(R_{10})_2$, $-C(O)R_{10}$, $-CO_2R_{10}$, $-S(O)_2N(R_{10})_2$, $-S(O)R_{10}$, $-S(O)_2OR_{10}$, $-S(O)_2R_{10}$; or has the formula 1a:

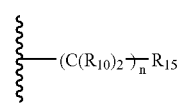

1a wherein independently for each occurrence of 1a;
n is 1, 2, 3, 4, 5, or 6;
$R_{15}$ is aryl, cycloalkyl, cycloalkenyl, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, or $-C(O)N(R_{10})_2$; or is a polycyclic ring containing 8-14 carbon atoms, of which one, two or three ring atoms are independently S, O or N;

or $A_1$ and $A_2$ taken together form $=O$ or $=S$; or $A_1$ and $A_2$ taken together with the carbon to which they are attached form a 5 to 8 membered heterocyclyl, of which one or two ring atoms are independently S, O or N;
B is O, S, $-(C=O)-$, $-(C=S)-$ or,

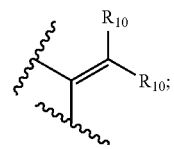

or has the formula 1b:

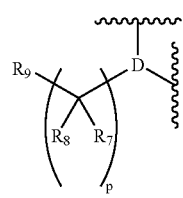

1b wherein
D is N or $CR_{10}$;
p is 0, 1, 2, 3, 4, or 5;
each of $R_7$ and $R_8$ is independently for each occurrence H, alkyl, alkenyl, alkynyl, aralkyl, aryl, cycloalkyl, heterocyclyl, cycloalkenyl, or heteroaryl; or $R_7$ and $R_8$ taken together form a 3-8 membered ring; or $R_7$ and $R_8$ taken together form a 4-8 membered ring;
$R_9$ is H, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, $-OCO_2R_{10}$, $-OC(O)N(R_{10})_2$, $-C(O)N(R_{10})_2$, halide, nitrile, nitro, or acylthio;
$R_1$ has the formula 1c:

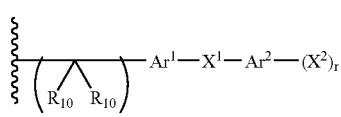

1c wherein
q is 1, 2, 3, 4, or 5;
r is 1, 2, 3, 4, or 5;
$Ar^1$ is a monocyclic or bicyclic aryl with 6-14 ring atoms; or a monocyclic or bicyclic heteroaryl with 5-14 ring atoms, of which one, two or three ring atoms are independently S, O or N; or $Ar^1$ is represented by formula 1d:

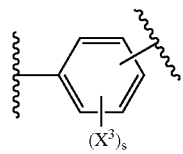

1d

Wherein s is 0, 1, 2, 3, or 4;

each of $X^2$ and $X^3$ is independently for each occurrence H, alkyl, alkenyl, alkynyl, aryl, cycloalkyl, heterocyclyl, aralkyl, heteroaryl, heteroaralkyl, hydroxyl, acyloxy, nitrile, nitro, halide, $OR_{11}$, $-C(O)N(R_{10})(R_{11})$, $-C(O)R_{11}$, $-CO_2R_{11}$, $-S(O)_2N(R_{10})(R_{11})$, $SR_{11}$, $-S(O)R_{11}$, $-S(O)_2OR_{11}$, $-S(O)_2R_{11}$, $-C(=NR_{10})N(R_{10})(R_{11})$, or $-C(=NR_{10})(R_{11})$; or has the formula 1a;

$Ar^2$ is a monocyclic or bicyclic aryl with 6-14 ring atoms; or a monocyclic or bicyclic heteroaryl with 5-14 ring atoms, of which one, two or three ring atoms are independently S, O or N;

$X^1$ is a bond, $-C(R_{10})_2-$, $-S-$, $-(NR_{10})-$, or $-O-$;

$R_2$ is H, a branched or unbranched alkyl or alkenyl, cycloalkyl, heterocyclyl, or bicycloalkyl; or has the formula 1a:

$R_3$ is H, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, $-OCO_2R_{10}$, $-OC(O)N(R_{10})_2$, $-C(O)N(R_{10})_2$, halide, nitrile, nitro, or acylthio;

each of $R_4$, $R_5$ and $R_{10}$ independently for each occurrence is H, alkyl, alkenyl, alkynyl, aralkyl, aryl, cycloalkyl, cycloalkenyl, bicycloalkyl, heterocyclyl, or heteroaryl; or has the formula 1a; or any two instances of $R_{10}$ taken together form a 3-8 membered ring; or $R_4$ and $R_5$ taken together form a 3-8 membered ring;

$R_6$ is H or alkyl;

$R_{11}$ is independently for each occurrence H, alkyl, alkenyl, alkynyl, aralkyl, aryl, cycloalkyl, cycloalkenyl, bicycloalkyl, heterocyclyl, heteroaryl, or $-[C(R_{12})(R_{13})]_t-R_{14}$;

wherein t is 0, 1, 2, 3, 4, or 5;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl.

Another aspect of the invention relates to a compound having the formula 10:

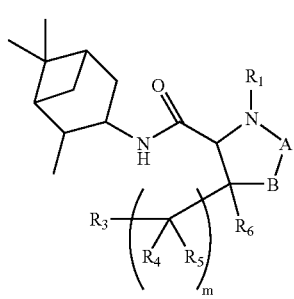

10 or an unsaturated form thereof or a pharmaceutically acceptable salt thereof;

wherein m represents independently for each occurrence 0, 1, 2, 3, 4, 5, or 6;

A is $-S(O)-$, $-S(O)_2-$,

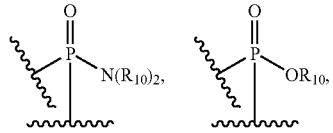

or $-C(A_1)(A_2)-$;

each of $A_1$ and $A_2$ is independently H, alkyl, alkenyl, alkynyl, aryl, cycloalkyl, aralkyl, heterocyclyl, heteroaryl, heteroaralkyl, $-C(O)N(R_{10})_2$, $-C(O)R_{10}$, $-CO_2R_{10}$, $-S(O)_2N(R_{10})_2$, $-S(O)R_{10}$, $-S(O)_2OR_{10}$, or $-S(O)_2R_{10}$; or has the formula 10a:

10a wherein independently for each occurrence of 10a;

n is 1, 2, 3, 4, 5, or 6; and $R_{15}$ is aryl, cycloalkyl, cycloalkenyl, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, or $-C(O)N(R_{10})_2$; or is a polycyclic ring containing 8-14 carbon atoms, of which one, two or three ring atoms are independently S, O or N;

or $A_1$ and $A_2$ taken together form =O or =S; or $A_1$ and $A_2$ taken together with the carbon to which they are attached form a 5 to 8 heterocyclyl, of which one or two ring atoms are independently S, O or N B is O, S, $-(C=O)-$, $-(C=S)-$ or,

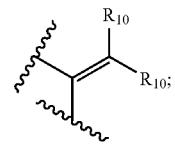

or has the formula 10b:

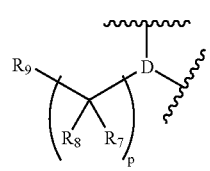

10b wherein

D is N or $CR_{10}$;

p is 0, 1, 2, 3, 4, or 5;

each of $R_7$ and $R_8$ is independently for each occurrence H, alkyl, alkenyl, alkynyl, aralkyl, aryl, cycloalkyl, heterocyclyl, cycloalkenyl, or heteroaryl; or $R_7$ and $R_8$ taken together form a 3-8 membered ring; or $R_7$ and $R_8$ taken together form a 4-8 membered ring;

$R_9$ is H, heterocyclyl, heteroaryl, —$OR_{10}$, —$SR_{10}$, —$N(R_{10})_2$, —$N(R_{10})CO_2R_{10}$, —$N(R_{10})C(O)N(R_{10})_2$, —$CO_2R_{10}$, —$OCO_2R_{10}$, —$OC(O)N(R_{10})_2$, —$C(O)N(R_{10})_2$, halide, nitrile, nitro, or acylthio;

$R_1$ has the formula 10c or 10d:

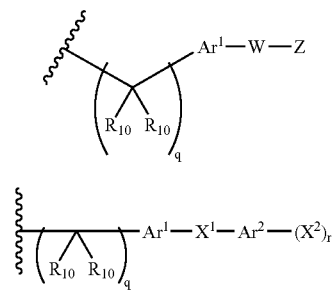

wherein q is 1, 2, 3, 4, or 5;

r is 1, 2, 3, 4, or 5;

W is a bond; or alkyl diradical, alkenyl diradical, or alkynyl diradical;

Z is H, —$SR_{10}$, —$S(O)_2R_{11}$, —$NR_{10}S(O)_2R_{11}$, —$S(O)R_{10}$, —$N(R_{10})(R_{11})$, —$C(O)R_{11}$, —$CO_2R_{11}$, —$C(O)N(R_{10})(R_{11})$, —$C(S)N(R_{10})(R_{11})$, —$CH_2C(O)$heterocyclyl, —$NR_{10}C(O)R_{11}$, —$NR_{10}CO_2R_{11}$, —$OC(O)N(R_{10})(R_{11})$, —$NC(O)CH(R_{10})(R_{11})$, —$C(=NR_{10})N(R_{10})(R_{11})$, —$C(=NR_{10})R_{11}$, hydroxyalkyl, monocyclic aryl, bicyclic aryl, heteroaryl, or heterocyclyl;

$Ar^1$ is a monocyclic or bicyclic aryl with 6-14 ring atoms; or a monocyclic or bicyclic heteroaryl with 5-14 ring atoms, of which one, two or three ring atoms are independently S, O or N; or $Ar^1$ is represented by formula 10e:

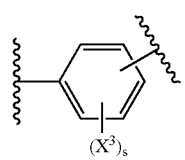

Wherein s is 0, 1, 2, 3, or 4;

each of $X^2$ and $X^3$ is independently for each occurrence H, alkyl, alkenyl, alkynyl, aryl, cycloalkyl, heterocyclyl, aralkyl, heteroaryl, heteroaralkyl, hydroxyl, acyloxy, nitrile, nitro, halide, $OR_{11}$, —$C(O)N(R_{10})(R_{11})$, —$C(O)R_{11}$, —$CO_2R_{11}$, —$S(O)_2N(R_{10})(R_{11})$, $SR_{11}$, —$S(O)R_{11}$, —$S(O)_2OR_{11}$, —$S(O)_2R_{11}$, —$C(=NR_{10})N(R_{10})(R_{11})$, or —$C(=NR_{10})(R_{11})$; or has the formula 10a;

$Ar^2$ represent independently for each occurrence are monocyclic or bicyclic aryl with 6-14 ring atoms; or a monocyclic or bicyclic heteroaryl with 5-14 ring atoms, of which one, two or three ring atoms are independently S, O or N;

$X^1$ is a bond, —$C(R_{10})_2$—, —S—, —$N(R_{10})$— or —O—;

$R_2$ is H, a branched or unbranched alkyl or alkenyl, cycloalkyl, heterocyclyl, orbicycloalkyl; or has the formula 10a:

$R_3$ is H, heterocyclyl, heteroaryl, —$OR_{10}$, —$SR_{10}$, —$N(R_{10})_2$, —$N(R_{10})CO_2R_{10}$, —$N(R_{10})C(O)N(R_{10})_2$, —$CO_2R_{10}$, —$OCO_2R_{10}$, —$OC(O)N(R_{10})_2$, —$C(O)N(R_{10})_2$, halide, nitrile, nitro, or acylthio;

each of $R_4$, $R_5$ and $R_{10}$ is independently for each occurrence H, alkyl, alkenyl, alkynyl, aralkyl, aryl, cycloalkyl, cycloalkenyl, bicycloalkyl, heterocyclyl, or heteroaryl; or has the formula 10a;

or any two instances of $R_{10}$ taken together form a 3-8 membered ring; or $R_4$ and $R_5$ taken together form a 3-8 membered ring;

$R_6$ is H or alkyl;

$R_{11}$ is independently for each occurrence H, alkyl, alkenyl, alkynyl, aralkyl, aryl, cycloalkyl, cycloalkenyl, bicycloalkyl, heterocyclyl, heteroaryl, or —$[C(R_{12})(R_{13})]_t$—$R_{14}$;

wherein t is 0, 1, 2, 3, 4, or 5;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl.

Another aspect of the invention relates to a compound represented by formula 14:

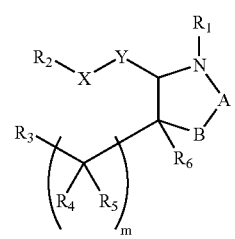

or an unsaturated form thereof or a pharmaceutically acceptable salt thereof;

wherein

Y is —$C(R_{10})_2$—, —(C=O)—, —(C=S)—, or —$C(=NR_{10})$—;

X is —$N(R_{10})$—, or a bond;

m represents independently for each occurrence 0, 1, 2, 3, 4, 5, or 6;

A is —S(O)—, —$S(O)_2$—,

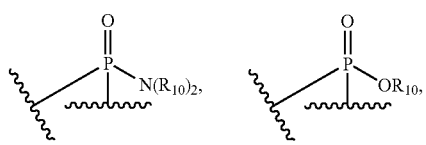

or —$C(A_1)(A_2)$—;

each of $A_1$ and $A_2$ is independently for each occurrence H, alkyl, alkenyl, alkynyl, aryl, cycloalkyl, aralkyl, heterocyclyl, heteroaryl, heteroaralkyl, —$C(O)N(R_{10})_2$, —$C(O)R_{10}$, —$CO_2R_{10}$, —$S(O)_2N(R_{10})_2$, —$S(O)R_{10}$, —$S(O)_2OR_{10}$, —$S(O)_2R_{10}$; or has the formula 14a:

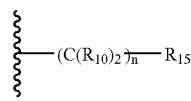

wherein independently for each occurrence of 14a;

n is 1, 2, 3, 4, 5, or 6; and $R_{15}$ is aryl, cycloalkyl, cycloalkenyl, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, or $-C(O)N(R_{10})_2$; or is a polycyclic ring containing 8-14 carbon atoms, of which one, two or three ring atoms are independently S, O or N;

or $A_1$ and $A_2$ taken together form $=O$ or $=S$; or $A_1$ and $A_2$ taken together with the carbon to which they are attached form a 5 to 8 heterocyclyl, of which one or two ring atoms are independently S, O or N;

B is $-(C(R)_2X)-$, $-(XC(R)_2)-$, or $-(C(R)_2)_2-$;

X independently for each occurrence is S, $-(NR_{10})-$, or $-O-$;

R independently for each occurrence is H, alkyl, alkenyl, alkynyl, aryl, cycloalkyl, aralkyl, heterocyclyl, heteroaryl, or heteroaralkyl; or has formula 14a;

$R_1$ has the formula 14b:

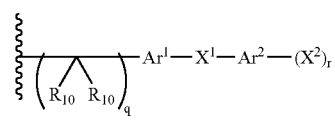

wherein q is 1, 2, 3, 4, or 5;

r is 0, 1, 2, 3, 4, or 5;

$Ar^1$ is a monocyclic or bicyclic aryl with 6-14 ring atoms; or a monocyclic or bicyclic heteroaryl with 5-14 ring atoms, of which one, two or three ring atoms are independently S, O or N; or $Ar^1$ is represented by formula 14c:

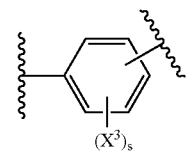

Wherein s is 0, 1, 2, 3, or 4;

each of $X^2$ and $X^3$ is independently for each occurrence H, alkyl, alkenyl, alkynyl, aryl, cycloalkyl, heterocyclyl, aralkyl, heteroaryl, heteroaralkyl, hydroxyl, acyloxy, nitrile, nitro, halide, $-OR_{11}$, $-C(O)N(R_{10})(R_{11})$, $-C(O)R_{11}$, $-CO_2R_{11}$, $-S(O)_2N(R_{10})(R_{11})$, $-SR_{11}$, $-S(O)R_{11}$, $-S(O)_2OR_{11}$, $-S(O)_2R_{11}$, $-C(=NR_{10})N(R_{10})(R_{11})$, or $-C(=NR_{10})(R_{11})$; or has the formula 14a;

$Ar^2$ represent independently for each occurrence are monocyclic or bicyclic aryl with 6-14 ring atoms; or a monocyclic or bicyclic heteroaryl with 5-14 ring atoms, of which one, two or three ring atoms are independently S, O or N;

$X^1$ is a bond, $-(C(R_{10})_2)-$, $-S-$, $-(NR_{10})-$, or $-O-$;

$R_2$ is H, a branched or unbranched alkyl or alkenyl, cycloalkyl, heterocyclyl, or bicycloalkyl; or has the formula 14a:

$R_3$ is H, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, $-OCO_2R_{10}$, $-OC(O)N(R_{10})_2$, $-C(O)N(R_{10})_2$, halide, nitrile, nitro, or acylthio;

each of $R_4$, $R_5$ and $R_{10}$ is independently for each occurrence H, alkyl, alkenyl, alkynyl, aralkyl, aryl, cycloalkyl, cycloalkenyl, bicycloalkyl, heterocyclyl, or heteroaryl; or has the formula 14a;

or any two instances of $R_{10}$ taken together form a 3-8 membered ring; or $R_4$ and $R_5$ taken together form a 3-8 membered ring;

$R_6$ is H or alkyl;

$R_{11}$ independently for each occurrence is H, alkyl, alkenyl, alkynyl, aralkyl, aryl, cycloalkyl, cycloalkenyl, bicycloalkyl, heterocyclyl, heteroaryl, or $-[C(R_{12})(R_{13})]_t-R_{14}$;

wherein t is 0, 1, 2, 3, 4, or 5;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl.

The compounds described above may have one or more of the following features (where applicable):

$Ar^2(X^2)_r$ is represented by the formula 3:

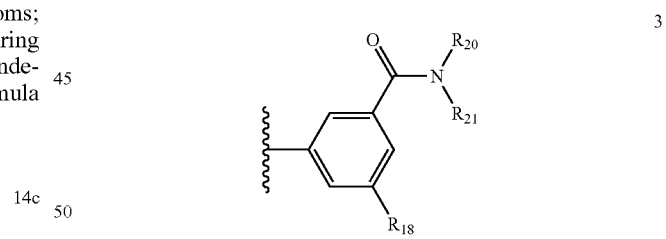

wherein $R_{18}$ is alkyl, alkenyl, halide, nitro, or amino;

each of $R_{20}$ and $R_{21}$ is independently H, alkyl, aralkyl, heteroaralkyl, alkoxy, or $-[C(R_{22})(R_{23})]_t-R_{24}$;

t is independently for each occurrence 0, 1, 2, 3, 4, or 5;

each of $R_{22}$ and $R_{23}$ is independently for each occurrence H, alkyl, aryl, aralkyl, cycloalkyl, heterocyclyl, heterocyclylalkyl, heteroaryl, or heteroaralkyl; and $R_{24}$ is independently for each occurrence H, alkyl, aryl, heteroaryl, heterocyclylalkyl, alkoxy, amino, amido, or carboxyl; Y is $-(C=O)-$ and X is $-NH-$; B has the formula 6a or 6b:

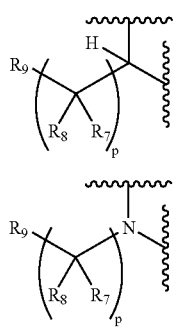

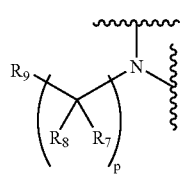

wherein
p is 0, 1, or 2;
each of $R_7$ and $R_8$ independently for each occurrence is H or alkyl; and
$R_9$ is H, —$OR_{10}$, —$N(R_{10})_2$, —$N(R_{10})CO_2R_{10}$, —$N(R_{10})C(O)N(R_{10})_2$, —$OCO_2R_{10}$, or —$OC(O)N(R_{10})_2$; B is S; $A_1$ and $A_2$ taken together form =O and B has the formula 8:

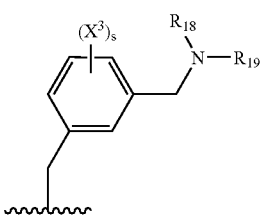

wherein
p is 0, 1 or 2;
each of $R_7$ and $R_8$ independently for each occurrence is H or alkyl; and
$R_9$ is H, —$OR_{10}$, —$N(R_{10})_2$, —$N(R_{10})CO_2R_{10}$, —$N(R_{10})C(O)N(R_{10})_2$, —$OCO_2R_{10}$, or —$OC(O)N(R_{10})_2$;
$A_1$ and $A_2$ are each H; $R_1$ has the formula 11:

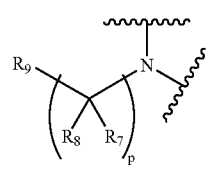

wherein
s is 0, 1, 2, 3, or 4;
each of $X^3$ is independently for each occurrence H or halide;
each of $R_{18}$ and $R_{19}$ is independently H, alkyl, alkenyl, alkynyl, aralkyl, aryl, cycloalkyl, cycloalkenyl, bicycloalkyl, heterocyclyl, heteroaryl, or —$[C(R_{12})(R_{13})]_t$—$R_{14}$;
wherein
t is 1, 2, 3, 4, or 5;
each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl; B has the formula 12a or 12b:

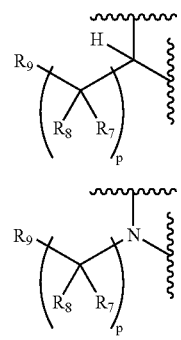

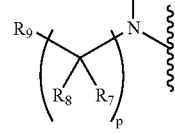

wherein
p is 0, 1, 2, 3, or 4;
each of $R_7$ and $R_8$ is independently for each occurrence H or alkyl; and
$R_9$ is H, —$OR_{10}$, —$N(R_{10})_2$, —$N(R_{10})CO_2R_{10}$, —$N(R_{10})C(O)N(R_{10})_2$, —$OCO_2R_{10}$, or —$OC(O)N(R_{10})_2$;
wherein A is —$C(A_1)(A_2)$-; $A_1$ and $A_2$ taken together form =O and B has the formula 13:

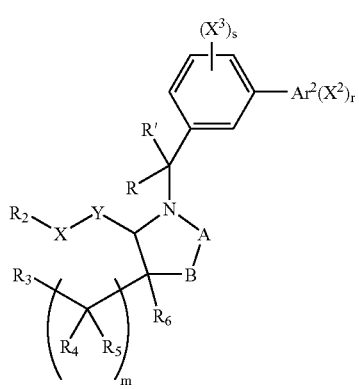

wherein
p is 0, 1, 2, 3, or 4;
each of $R_7$ and $R_8$ independently for each occurrence is H or alkyl; and
$R_9$ is H, —$OR_{10}$, —$N(R_{10})_2$, —$N(R_{10})CO_2R_{10}$, —$N(R_{10})C(O)N(R_{10})_2$, —$OCO_2R_{10}$, or —$OC(O)N(R_{10})_2$;
and $R_2$ is bicycloalkyl.

The compound may have the structure 2:

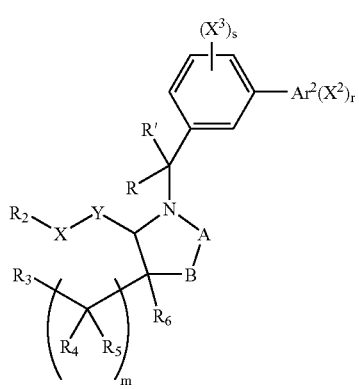

wherein
Y is —C(R$_{10}$)$_2$—, —(C=O)—, or —(C=S)—;
X is —N(R$_{10}$)—;
m is 0, 1, 2, or 3;
r is 1, 2, 3, 4, or 5;
s is 0, 1, 2, 3, or 4;
A is —S(O)—, —S(O)$_2$—,

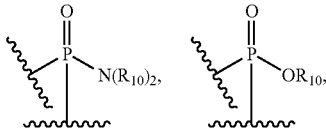

or —C(A$_1$)(A$_2$)-;
each of A$_1$ and A$_2$ is independently H, alkyl, aryl, cycloalkyl, aralkyl, heterocyclyl, heteroaryl, heteroaralkyl, —C(O)N(R$_{10}$)$_2$, —C(O)R$_{10}$, —CO$_2$R$_{10}$, —S(O)$_2$N(R$_{10}$)$_2$, —S(O)R$_{10}$, —S(O)$_2$OR$_{10}$, or —S(O)$_2$R$_{10}$; or has the formula 2a:

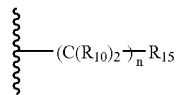

wherein independently for each occurrence of 2a;
n is 1, 2, 3, 4, 5, or 6;
R$_{15}$ is aryl, cycloalkyl, cycloalkenyl, heterocyclyl, heteroaryl, —OR$_{10}$, —SR$_{10}$, —N(R$_{10}$)$_2$, —N(R$_{10}$)CO$_2$R$_{10}$, —N(R$_{10}$)C(O)N(R$_{10}$)$_2$, —CO$_2$R$_{10}$, or —C(O)N(R$_{10}$)$_2$; or is a polycyclic ring containing 8-14 carbon atoms, of which one, two or three ring atoms are independently S, O or N;
or A$_1$ and A$_2$ taken together form =O or =S;
B is —(C=O)—, —(C=S)—, O, or S; or has the formula 2b:

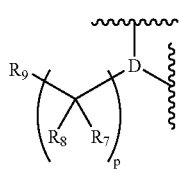

wherein
D is N or CR$_{10}$;
p is 0, 1, 2, or 3;
each of R$_7$ and R$_8$ is independently for each occurrence H, alkyl, alkenyl, alkynyl, aralkyl, aryl, cycloalkyl, heterocyclyl, cycloalkenyl, or heteroaryl; or R$_7$ and R$_8$ taken together form a 3-8 membered ring; or R$_7$ and R$_8$ taken together form a 4-8 membered ring;
R$_9$ is H, heterocyclyl, heteroaryl, —OR$_{10}$, —SR$_{10}$, —N(R$_{10}$)$_2$, —N(R$_{10}$)CO$_2$R$_{10}$, —N(R$_{10}$)C(O)N(R$_{10}$)$_2$, —CO$_2$R$_{10}$, —OCO$_2$R$_{10}$, —OC(O)N(R$_{10}$)$_2$, —C(O)N(R$_{10}$)$_2$, halide, nitrile, nitro, or acylthio;
Ar$^2$ is a monocyclic or bicyclic aryl with 6-10 ring atoms; or a monocyclic or bicyclic heteroaryl with 5-14 ring atoms, of which one, two or three ring atoms are independently S, O or N;
X$^2$ is independently for each occurrence H, alkyl, alkenyl, alkynyl, aryl, cycloalkyl, heterocyclyl, aralkyl, heteroaryl, heteroaralkyl, hydroxyl, acyloxy, nitrile, nitro, halide, OR$_{11}$, —C(O)N(R$_{10}$)(R$_{11}$), —C(O)R$_{11}$, —CO$_2$R$_{11}$, —S(O)$_2$N(R$_{10}$)(R$_{11}$), SR$_{11}$, —S(O)R$_{11}$, —S(O)$_2$OR$_{11}$, —S(O)$_2$R$_{11}$, —C(=NR$_{10}$)N(R$_{10}$)(R$_{11}$), or —C(=NR$_{10}$)(R$_{11}$); or has the formula 2a;
each of R$_4$, R$_5$ and R$_{10}$ is independently for each occurrence H, alkyl, alkenyl, alkynyl, aralkyl, aryl, cycloalkyl, cycloalkenyl, bicycloalkyl, heterocyclyl, or heteroaryl; or has the formula 2a; or any two instances of R$_{10}$ taken together form a 3-8 membered ring; or R$_4$ and R$_5$ taken together form a 3-8 membered ring;
X$^3$ is independently for each occurrence H, alkyl, alkenyl, —OR$_{11}$, or halide; or has formula 2a;
each of R and R' is independently for each occurrence H or alkyl;
R$_6$ is H or alkyl;
R$_{11}$ is independently for each occurrence H, alkyl, alkenyl, alkynyl, aralkyl, aryl, cycloalkyl, cycloalkenyl, bicycloalkyl, heterocyclyl, heteroaryl, or —[C(R$_{12}$)(R$_{13}$)]$_t$—R$_{14}$;
wherein
t is independently for each occurrence 0, 1, 2, 3, 4, or 5;
each of R$_{12}$ and R$_{13}$ is independently for each occurrence H, alkyl, aryl, aralkyl, cycloalkyl, heterocyclyl, heterocyclylalkyl, heteroaryl, or heteroaralkyl; and
R$_{14}$ is independently for each occurrence H, alkyl, aryl, heteroaryl, heterocyclylalkyl, alkoxy, amino, amido, or carboxyl.

Alternatively, the compound may have the formula 4

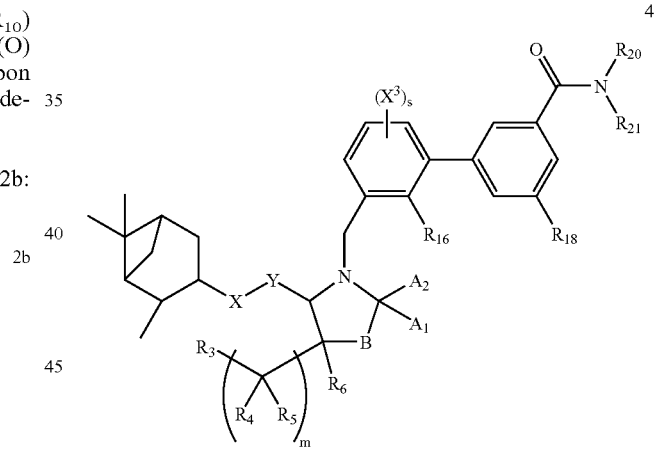

wherein
Y is —C(R$_{10}$)$_2$—, —(C=O)—, or —(C=S)—;
X is —N(R$_{10}$)—;
m is 0, 1, 2, 3, or 4;
s is 0, 1, 2, 3;
each of A$_1$ and A$_2$ is independently H, alkyl, aryl, cycloalkyl, aralkyl, heterocyclyl, heteroaryl, heteroaralkyl, —C(O)N(R$_{10}$)$_2$, —C(O)R$_{10}$, —CO$_2$R$_{10}$, —S(O)$_2$N(R$_{10}$)$_2$, —S(O)R$_{10}$, —S(O)$_2$OR$_{10}$, or —S(O)$_2$R$_{10}$; or has the formula 4a:

wherein independently for each occurrence of 4a;

n is 1, 2, 3, 4, 5, or 6; and $R_{15}$ is aryl, cycloalkyl, cycloalkenyl, heterocyclyl, heteroaryl, —$OR_{10}$, —$SR_{10}$, —$N(R_{10})_2$, —$N(R_{10})CO_2R_{10}$, —$N(R_{10})C(O)N(R_{10})_2$, —$CO_2R_{10}$, or —$C(O)N(R_{10})_2$; or is a polycyclic ring containing 8-14 carbon atoms, of which one, two or three ring atoms are independently S, O or N;

or $A_1$ and $A_2$ taken together form =O or =S;

B is O, S, —(C=O)—, or —(C=S)—; or has the formula 4b:

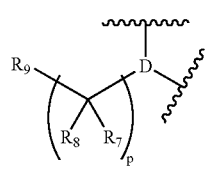

wherein

D is N or $CR_{10}$;

p is 0, 1, 2, 3;

each of $R_7$ and $R_8$ is independently for each occurrence H, alkyl, alkenyl, alkynyl, aralkyl, aryl, cycloalkyl, heterocyclyl, cycloalkenyl, or heteroaryl; or $R_7$ and $R_8$ taken together form a 3-8 membered ring; or $R_7$ and $R_8$ taken together form a 4-8 membered ring;

$R_9$ is H, heterocyclyl, heteroaryl, —$OR_{10}$, —$SR_{10}$, —$N(R_{10})_2$, —$N(R_{10})CO_2R_{10}$, —$N(R_{10})C(O)N(R_{10})_2$, —$CO_2R_{10}$, —$OCO_2R_{10}$, —$OC(O)N(R_{10})_2$, —$C(O)N(R_{10})_2$, halide, nitrile, nitro, or acylthio;

$R_6$ is H or alkyl;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl;

$R_{14}$ is independently for each occurrence H, alkyl, aryl, heteroaryl, heterocyclylalkyl, alkoxy, amino, amido, or carboxyl;

$R_{16}$ is H, alkyl, alkenyl, or $OR_{11}$; has the formula 4a;

each of $X^3$ independently for each occurrence is H or halide;

$R_{18}$ is alkyl, alkenyl, halide, nitro, or amino;

each of $R_{20}$ and $R_{21}$ is independently H, alkyl, aralkyl, heteroaralkyl, alkoxy, or —$[C(R_{22})(R_{23})]_t$—$R_{24}$;

t is independently for each occurrence 1, 2, 3, 4, or 5;

each of $R_{22}$ and $R_{23}$ is independently for each occurrence H, alkyl, aryl, aralkyl, cycloalkyl, heterocyclyl, heterocyclylalkyl, heteroaryl, or heteroaralkyl; and $R_{24}$ is independently for each occurrence H, alkyl, aryl, heteroaryl, heterocyclylalkyl, alkoxy, amino, amido, or carboxyl.

Specific compounds include those shown below:

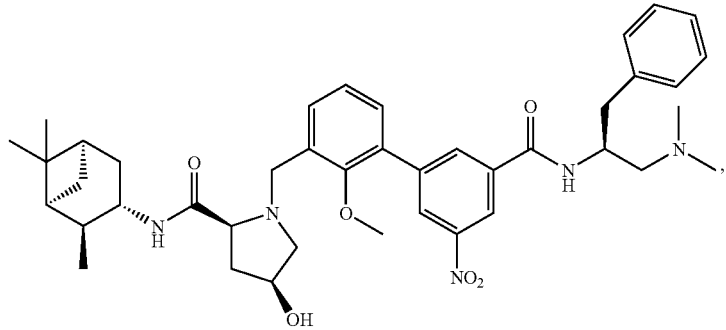

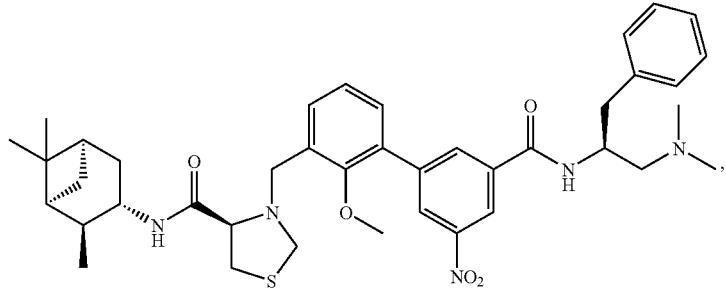

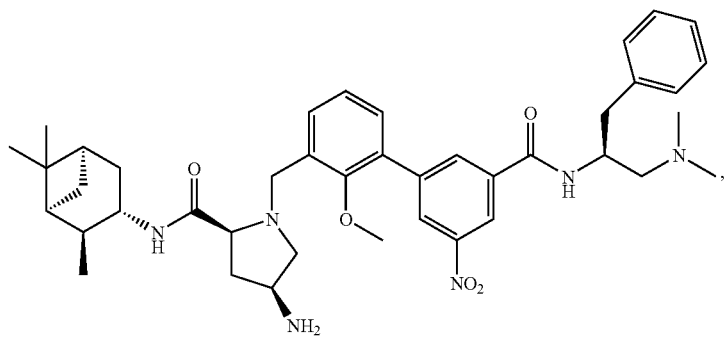

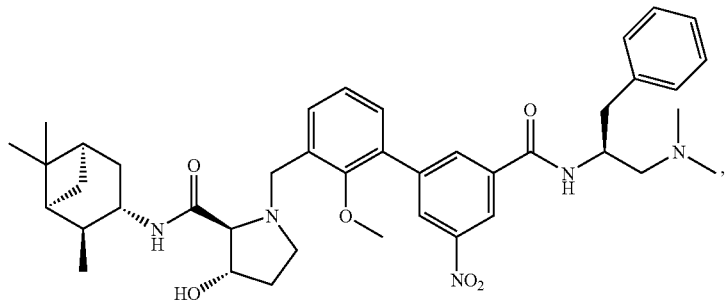
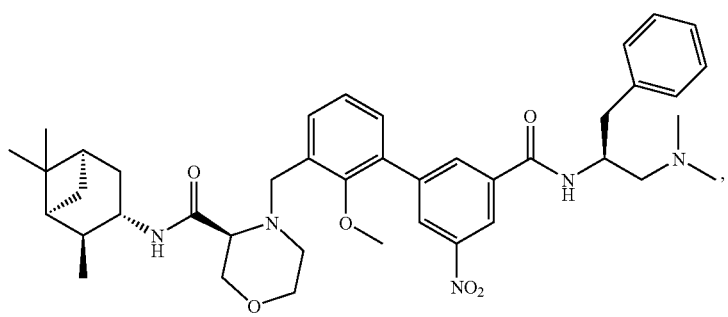
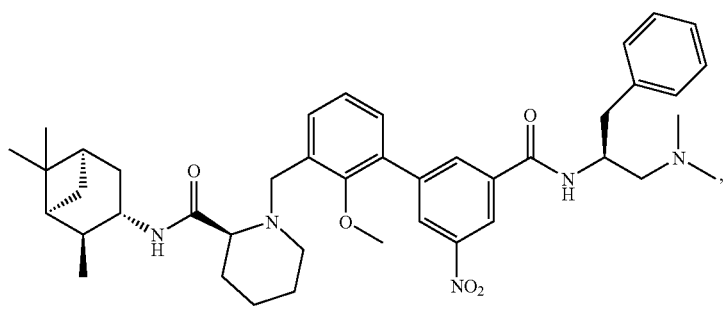
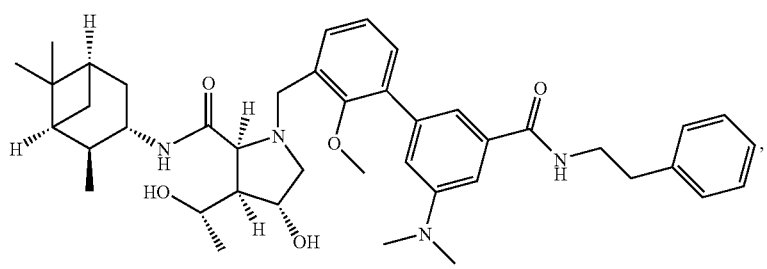
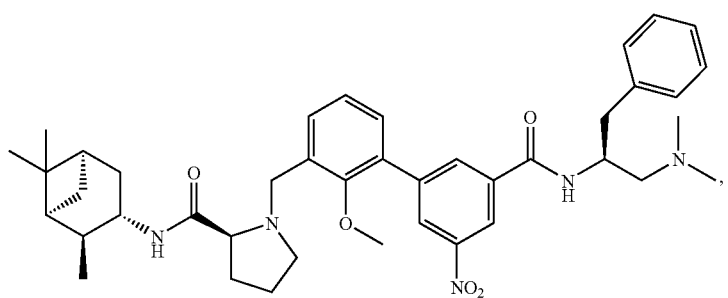

-continued
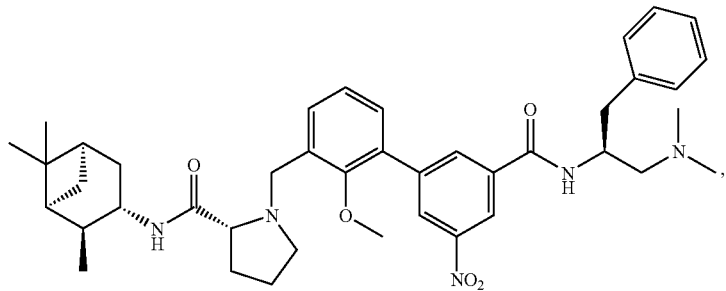
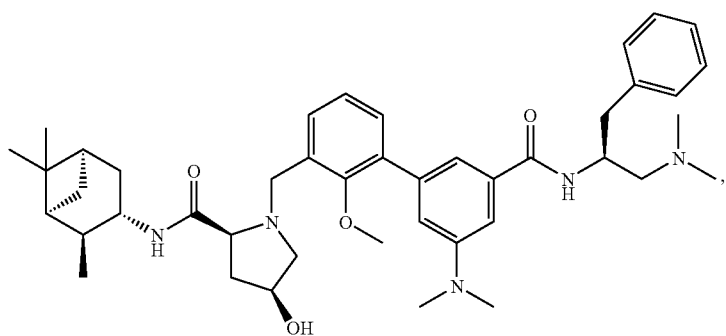
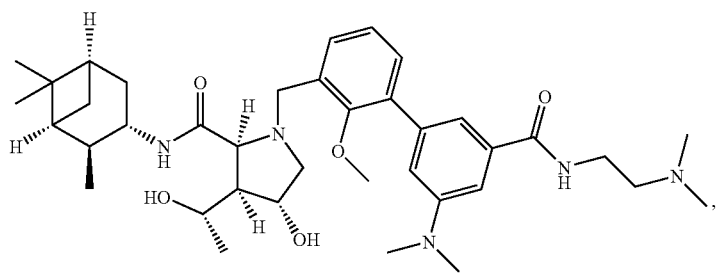
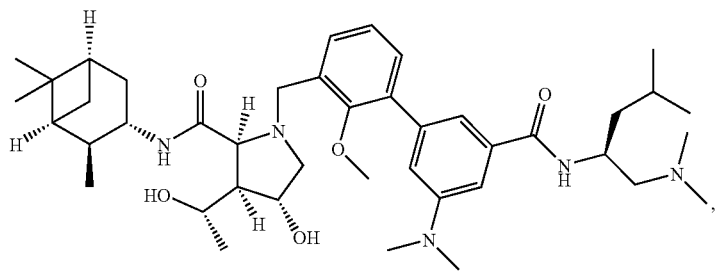
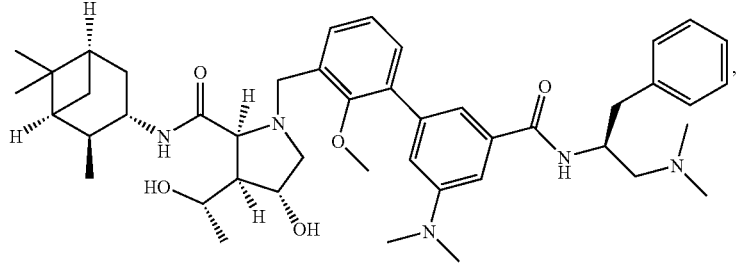

-continued
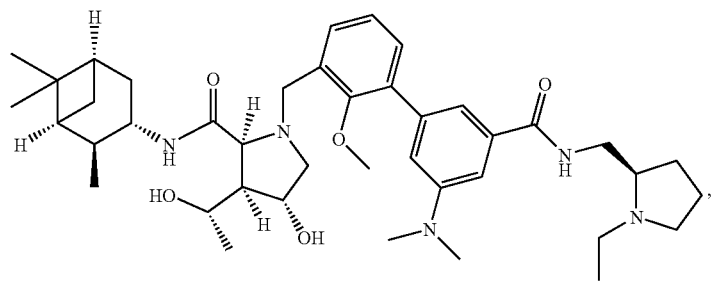
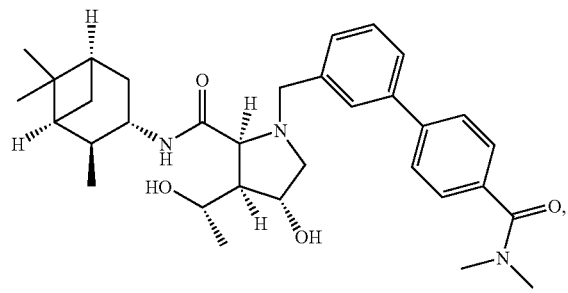
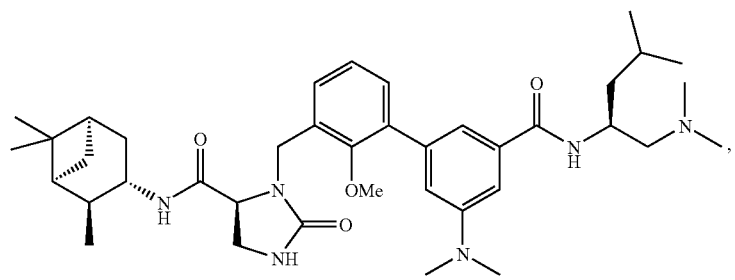
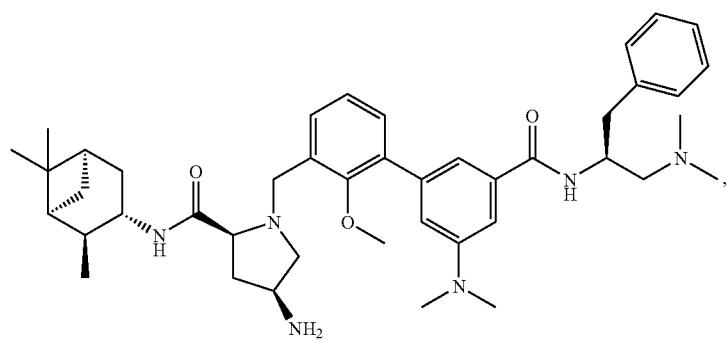
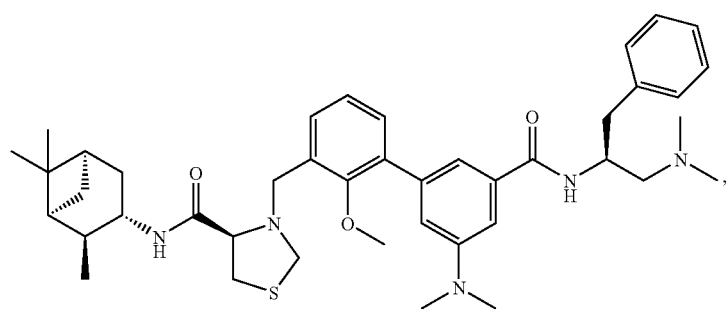

-continued

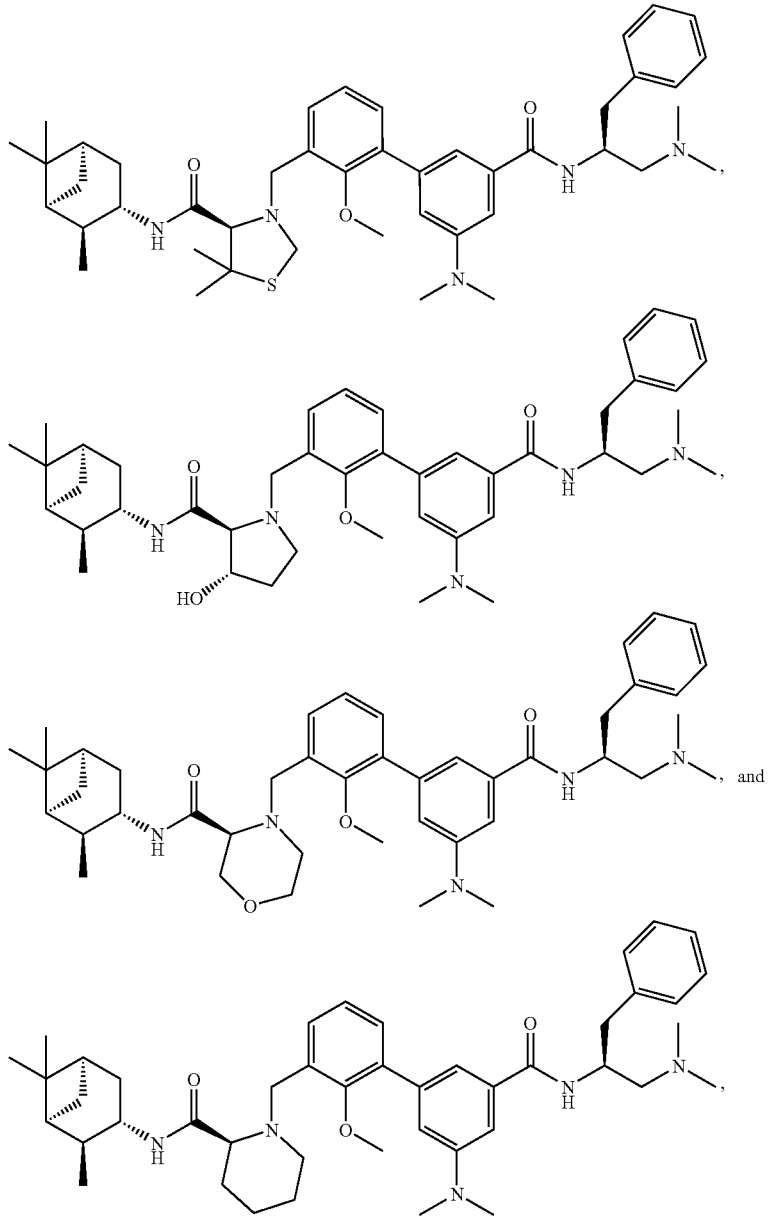

Methods of the Invention

One aspect of the present invention relates to a method of treating a Bcl-mediated disorder, comprising the step of: administering to a patient in need thereof a therapeutically effective amount of a compound of formula 1, 10, or 14, or a salt thereof as described above. In another aspect, the present invention relates to a method of treating a Bcl-mediated disorder, comprising the step of: administering to a patient in need thereof a therapeutically effective amount of a chemotherapeutic agent in combination with a therapeutically effective amount of a compound of compound of formula 1, 10, or 14, or a salt thereof as described above.

In certain embodiments of either aspect, the Bcl-mediated disorder is cancer or neoplastic disease. The cancer or neoplastic disease can be selected from the group consisting of acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia Vera, Hodgkin's disease, non-Hodgkin's disease; multiple myeloma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and endometrial cancer.

The cancer can also be follicular lymphoma, diffuse large B-cell lymphoma, mantle cell lymphoma, chronic lymphocytic leukemia prostrate cancer, breast cancer, neuroblastoma, colorectal, endometrial, ovarian, lung cancer, hepatocellular carcinoma, multiple myeloma, head and neck or testicular cancer.

In certain embodiments, the cancer over-expresses a Bcl protein and/or is dependent upon a Bcl protein for growth and survival. The Bcl protein can be, e.g., Bcl-2 or Bcl-xL. In other embodiments, the cancer exhibits a t(14; 18) chromosomal translocation.

The compound can be administered parenterally, intramuscularly, intravenously, subcutaneously, orally, pulmonary, intrathecally, topically or intranasally. In certain embodiments, the compound is administered systemically. In certain embodiments, the patient is a mammal, preferably a primate, more preferably a human.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which may be combined with a carrier material to produce a single dosage form will vary depending upon the host being treated, the particular mode of administration. The amount of active ingredient which may be combined with a carrier material to produce a single dosage form will generally be that amount of the compound which produces a therapeutic effect. Generally, out of one hundred per cent, this amount will range from about 0.1 percent to about ninety-nine percent of active ingredient, preferably from about 5 percent to about 70 percent, most preferably from about 10 percent to about 30 percent.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles, and/or as mouth washes and the like, each containing a predetermined amount of a compound of the present invention as an active ingredient.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which may be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissue.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms may be made by dissolving or dispersing the compound in the proper medium. Absorption enhancers can also be used to increase the flux of the compound across the skin. The rate of such flux may be controlled by either providing a rate controlling membrane or dispersing the compound in a polymer matrix or gel.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Ophthalmic formulations, eye ointments, powders, solutions and the like, are also contemplated as being within the scope of this invention.

When the compounds of the present invention are administered as pharmaceuticals, to humans and animals, they may be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

EXEMPLIFICATION

The invention now being generally described, it will be more readily understood by reference to the following examples, which are included merely for purposes of illustration of certain aspects and embodiments of the present invention, and are not intended to limit the invention.

Example 1

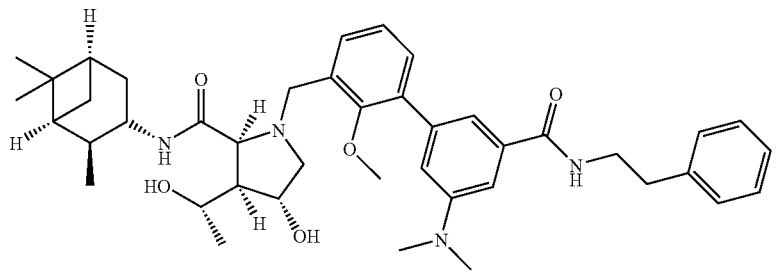

Part A

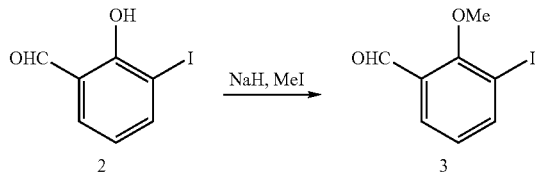

To a solution of phenol 2 (750 mg, 3 mmol, 1 eq) in DMF (5 mL) at 0° C. was added NaH (130 m g, 3.6 mmol, 1.2 eq) followed by MeI (280 μL, 4.5 mmol, 1.5 eq). The reaction mixture was stirred at rt for 24 h and then quenched with water. The mixture was diluted with EtOAc and washed with water (twice) then brine. The solution was dried over MgSO$_4$, filtered and concentrated to afford 795 mg (100%) of crude product 3.

Part B

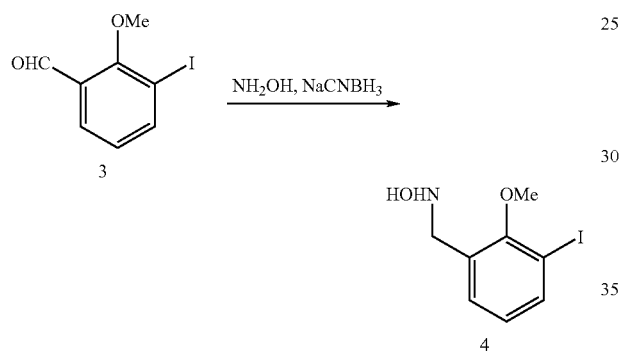

Aldehyde 3 (795 mg, 3.03 mmol, 1 eq) and hydroxylamine hydrochloride (253 mg, 3.64 mmol, 1.2 eq) were dissolved in THF/MeOH (3:2, 10 mL). Water (2 mL) was added and the pH was adjusted to 9 with 6.0 N KOH. The reaction mixture was stirred at rt overnight. After 16 h, sodium cyanoborohydride (381 mg, 6.07 mmol, 2 eq) was added followed by a crystal of methyl orange. The pH was adjusted to 2 and the resulting ruby red color was maintained for the duration of the reaction by the frequent addition of 1 N HCl. After stirring for 2 h another portion of sodium cyanoborohydride (381 mg) was added. After stirring for a total of 16 h, the pH of the reaction mixture was brought to 7 and DCM was added. The mixture was washed with water (three times), brine and then dried over MgSO$_4$. The crude product was purified by flash chromatography (50% EtOAc in hexanes then 100% EtOAc) to afford 706 mg (83%) of hydroxylamine 4.

Part C

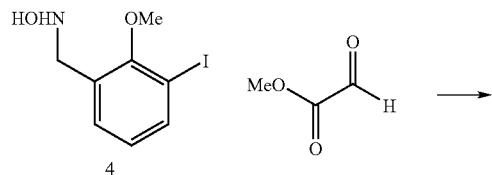

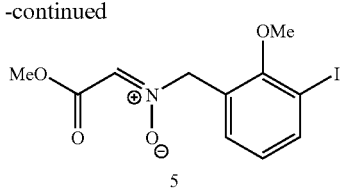

A solution of hydroxylamine 4 (705 mg, 2.53 mmol, 1 eq) and methyl glyoxylate (445 mg, 5.05 mmol, 2 eq) in benzene (15 mL) was heated at reflux with a Dean Stark trap overnight. Excess solvent was removed under reduced pressure and the resulting nitrone 5 was taken on crude in the next step.

Part D

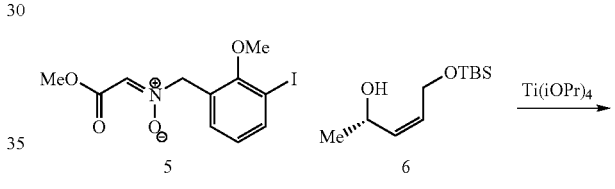

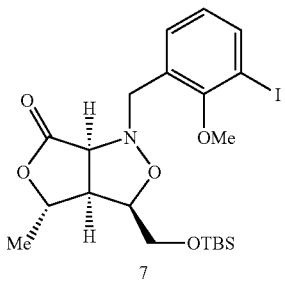

Nitrone 5 (882 mg, 2.53 mmol, 1 eq), allylic alcohol 6 (U.S. Ser. No. 11/156,364, filed Jun. 17, 2005) (820 mg, 3.79 mmol, 1.5 eq) and Ti(iOPr)$_4$ (1.12 mL, 3.79 mmol, 1.5 eq) were dissolved in toluene (5 mL) and heated in the microwave at 120° C. for 10 min The reaction mixture was diluted with EtOAc (15 mL) and 3-(dimethylamino)-1,2-propanediol (500 μL) was added. After stirring for 2 h, EtOAc was added and the mixture was washed with water (three times) then brine, dried over MgSO$_4$, filtered over Celite and concentrated. The crude residue was purified by flash chromatography (5:1 hexanes/EtOAc) to afford 575 mg (43%) of lactone 7.

Part E

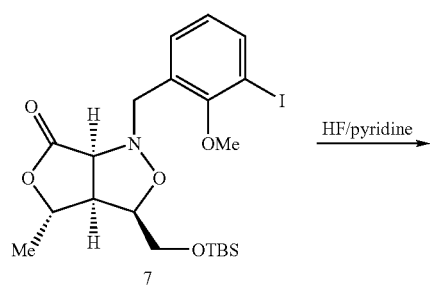

To a solution of 7 (225 mg, 0.042 mmol, 1 eq) in THF (6 mL) was added pyridine (2 mL) and HF/pyridine (2 mL). The mixture was stirred at rt for 4 h then TMSOMe (8 mL) was added. Solvent was removed under reduced pressure and the crude product was purified by flash chromatography (EtOAc) to afford 128 mg (72%) of 8 as a white foam.

Part F

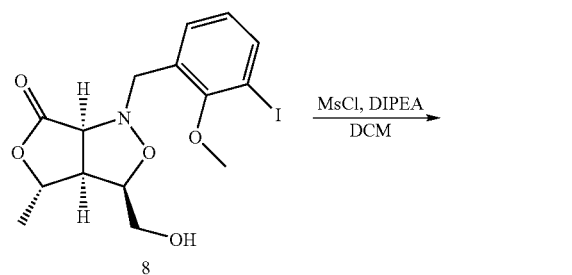

To a 0° C. solution of lactone 8 (0.94 g, 2.2 mmol, 1 eq) in DCM (22 mL) was added triethylamine (0.68 mL, 4.9 mmol, 2.2 eq) followed by the dropwise addition of methanesulfonyl chloride (0.38 mL, 4.9 mmol, 2.2 eq). The reaction mixture was allowed to warm to rt over 12 h, after which TLC and LC/MS confirmed complete consumption of alcohol. The mixture was then poured into DCM (100 mL) and a saturated sodium bicarbonate solution (25 mL). The layers were separated and the aqueous layer was extracted with DCM (3×30 mL). The combined organic extracts were dried (MgSO$_4$), filtered and concentrated in vacuo. The crude material was purified by gradient flash chromatography (100 g SiO$_2$, 30-70% EtOAc/Hex) to afford 9 (1.04 g, 2.1 mmol, 94%).

Part G

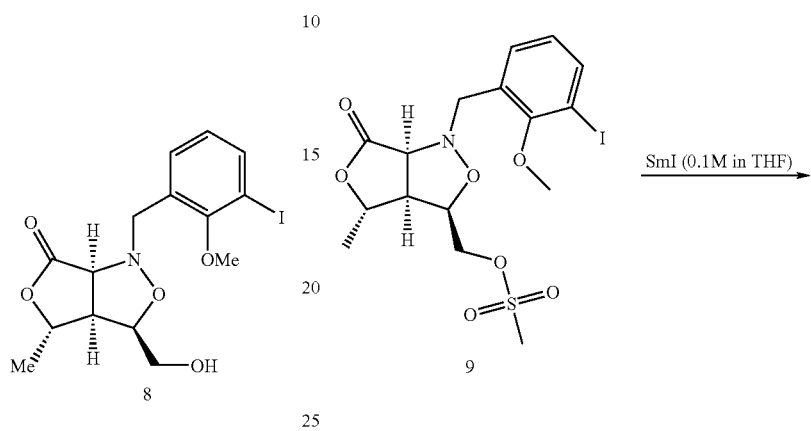

To neat mesylate 9 (450 mg, 0.91 mmol) at rt was added samarium iodide (27 mL of a 0.1 M THF solution, 2.7 mmol). After stirring at rt for 1 h, the reaction was quenched with a 5% ammonium chloride solution (10 mL) which resulted in an immediate color change of the reaction mixture from dark blue to yellow. The reaction mixture was then filtered through a pad of celite and the filtrate was diluted with water (100 mL) and EtOAc (100 mL). The aqueous layer was extracted with EtOAc (2×50 mL). The combined organic extracts were washed with brine (50 mL), dried (MgSO$_4$), filtered and concentrated in vacuo. The crude material was purified by gradient flash chromatography (75 g SiO$_2$, 30-80% EtOAc/Hex) to afford 10 (190 mg, 2.1 mmol, 52% yield).

Part H

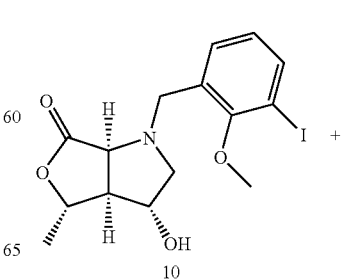

-continued

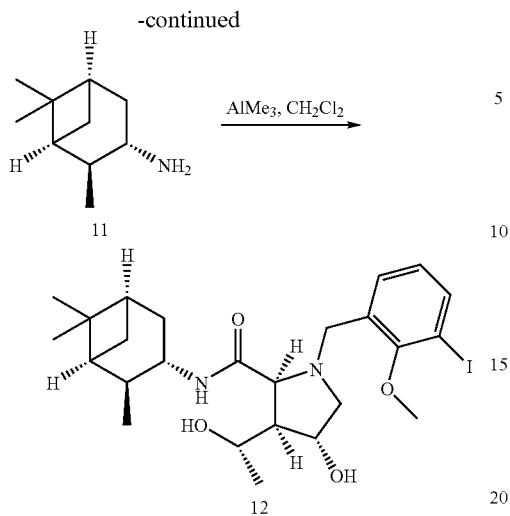

To a rt solution of (+)-isopinocampheylamine 11 (0.25 mL, 1.5 mmol) in DCM (2 mL) was added AlMe$_3$ (0.71 mL of a 2 M solution in hexane, 1.4 mmol). After stirring for 10 min, a solution of lactone 10 (190 mg, 0.47 mmol) in DCM (3 mL) was added and the mixture was stirred at rt. After stirring for 16 h, the reaction was quenched with a saturated aqueous Rochelle Salt solution (5 mL) and vigorously stirred at 23° C. for 2 h until a clear biphasic mixture appeared. The aqueous layer was separated and extracted with DCM (2×25 mL). The combined organic extracts were washed with brine (10 mL), dried (MgSO$_4$), filtered and concentrated in vacuo. The crude material was purified by gradient flash chromatography (50 g SiO$_2$, 2-5% MeOH/DCM) to afford 201 mg (77%) of 12 as a yellow oil.

Part I

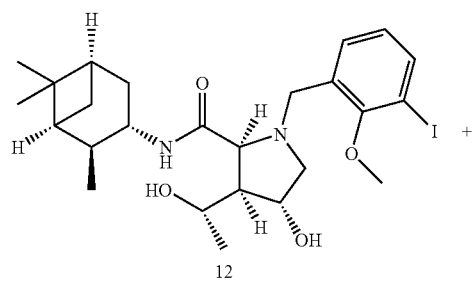

-continued

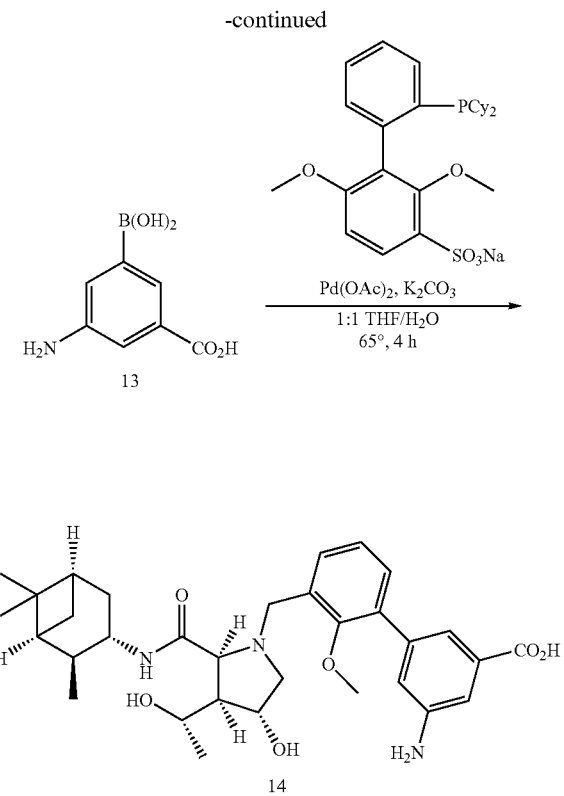

To a degassed (Ar) solution of pyrrolidine 12 (190 mg, 0.34 mmol) in a THF/H$_2$O mixture (1:1, 4 mL) was added boronic acid 13 (120 mg, 0.68 mmol), palladium acetate (12 mg, 0.05 mmol), potassium carbonate (190 mg, 1.4 mmol) and finally phosphine ligand (Anderson, K. W.; et. al., Angew. Chemie 2005, 44, 2922) (54 mg, 0.1 mmol). The reaction was heated to 65° C. After 4 h at 65° C., the reaction mixture was allowed to cool to 23° C. over the course of an hour, diluted with DCM and filtered through a pad of sand and celite. The filtrate was then extracted using DCM (50 mL) from a pH 4 water solution (20 mL). The aqueous layer was separated and extracted with DCM (2×20 mL), the combined organic extracts were washed with brine (15 mL), dried (MgSO$_4$), filtered and concentrated in vacuo. The crude residue was used in the subsequent reaction without further purification.

Part J

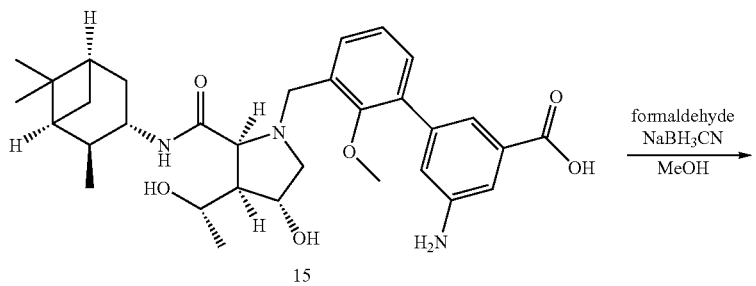

-continued

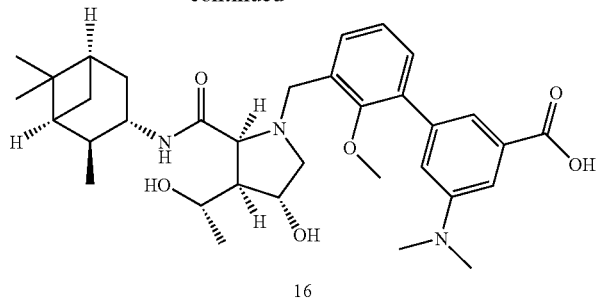

16

To a solution of crude pyrrolidine 15 (190 mg, 0.34 mmol) in MeOH (4 mL) was added formaldehyde (41 uL of a 37% aqueous solution, 1.37 mmol) followed by sodium cyanoborohydride (43 mg, 0.68 mmol) in a single portion.

After stirring for 12 h at 23° C., the reaction solution was concentrated in vacuo. The crude material was purified by gradient-flash chromatography (75 g SiO$_2$, 2-10% MeOH/DCM) to afford 130 mg (64% over 2 steps) of 16 as a white solid.

Part K

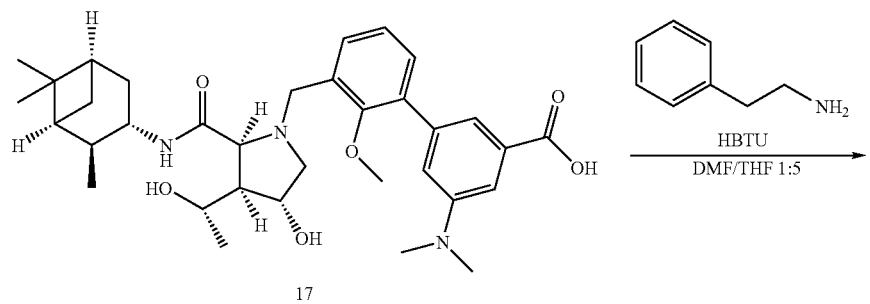

17

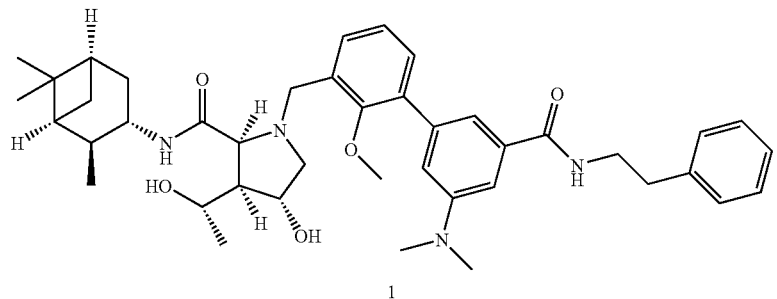

1

To a solution of pyrrolidine 17 (11 mg, 0.02 mmol) in THF/DMF (4:1, 1 mL) was added HBTU (10 mg, 0.04 mmol) followed by the addition of phenethylamine (5 uL, 0.04 mmol). After stirring at 23° C. for 1 h, the reaction mixture was diluted with methanol (0.5 mL) and purified directly on a prep reverse phase HPLC, using aqueous 40 mM ammonium bicarbonate/acetonitrile gradient as eluent to yield 5 mg (40%) of 1. MS (ESI(+)) m/z 697.3. (M+H)$^+$.

Example 2

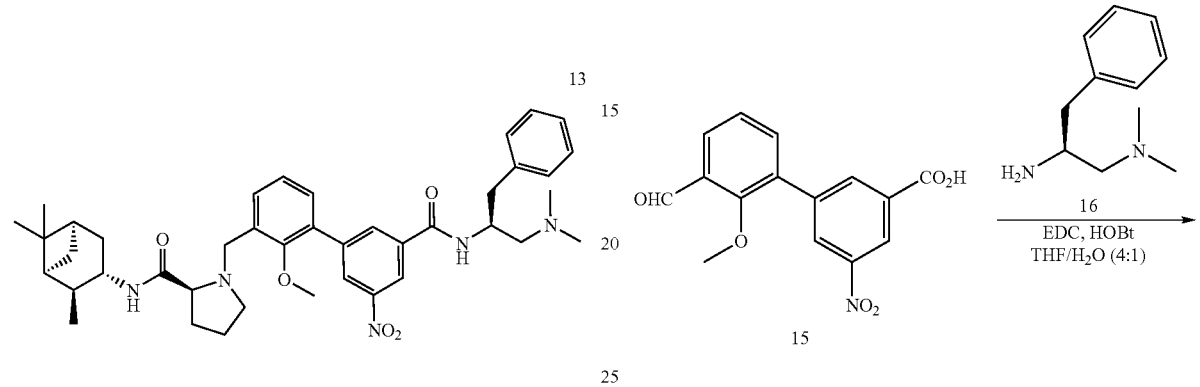

Part A

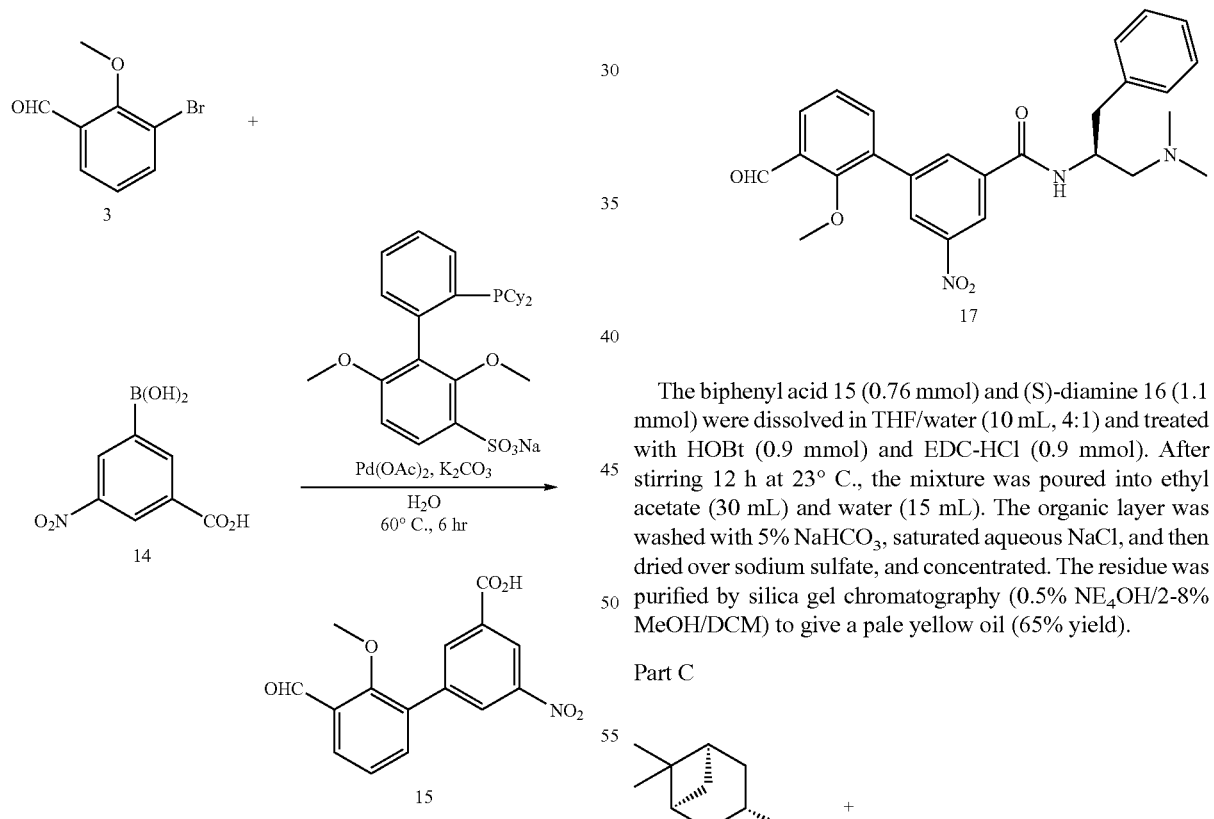

Under argon atmosphere, aryl bromide 3 (2.32 mmol), boronic acid 14 (2.8 mmol), phosphine ligand (0.1 mmol), palladium acetate (0.5 mmol), and potassium carbonate (9.3 mmol) were suspended in degassed water and heated with stirring at 60° C. for 8 h (K. W. Anderson and S. L. Buchwald, *Ang. Chem. Int. Ed.*, 2005, 44, 2). The mixture was poured into DCM (40 mL) and water (20 mL), and the pH of the aqueous layer was adjusted to 3 with 2N HCl. The layers were mixed and separated, and the aqueous layer was extracted with DCM (20 mL). The organic layers were combined, washed with saturated aqueous NaCl, dried over sodium sulfate, and concentrated to a light yellow oil. Purification by silica gel chromatography (0.5% HOAc/20-40% ethyl acetate/hexanes) yielded pale yellow solid (33% yield).

Part B

The biphenyl acid 15 (0.76 mmol) and (S)-diamine 16 (1.1 mmol) were dissolved in THF/water (10 mL, 4:1) and treated with HOBt (0.9 mmol) and EDC-HCl (0.9 mmol). After stirring 12 h at 23° C., the mixture was poured into ethyl acetate (30 mL) and water (15 mL). The organic layer was washed with 5% NaHCO$_3$, saturated aqueous NaCl, and then dried over sodium sulfate, and concentrated. The residue was purified by silica gel chromatography (0.5% NE$_4$OH/2-8% MeOH/DCM) to give a pale yellow oil (65% yield).

Part C

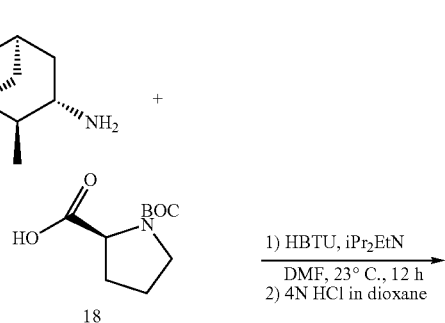

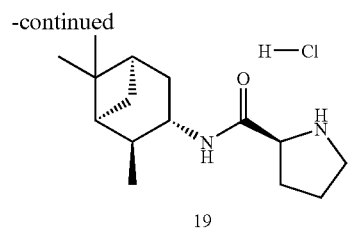

19

Boc-L-proline 18 (0.46 mmol) and (+)-isopinocamphylamine (0.46 mmol) with diisopropylethylamine are dissolved in DMF (2 mL) and DCM (1 mL) and treated with HBTU (0.46 mmol). The mixture is stirred at 23° C. for 12 h and then poured into ether (40 mL) and water (20 mL). The organic layer is washed with additional water (20 mL), 5% NaHCO$_3$, 1N HCl, saturated aqueous NaCl, and then dried over MgSO$_4$. The oil produced from concentration is restored in ether (5 mL) and stirred with HCl in dioxane (4 N, 5 mL) for 4 h. The solution is concentrated in vacuo and dried to produce a white solid. (80% yield)

Part D

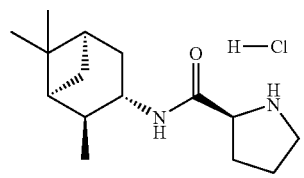

19

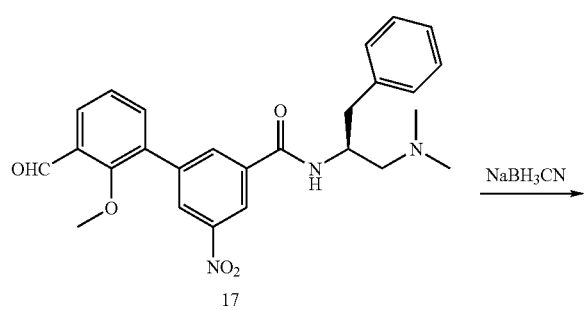

17

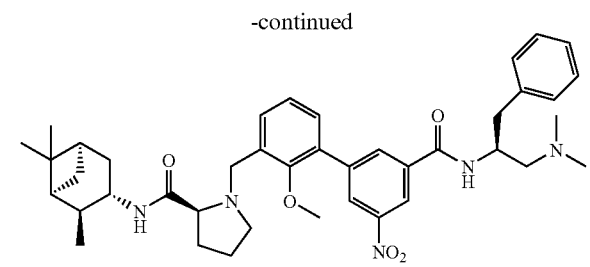

13

The amine 19 (0.16 mmol) and aldehyde 17 (0.54 mmol) were dissolved in methanol (1.2 mL) and treated with acetic acid (0.05 mL) and sodium cyanoborohydride (0.16 mmol). After stirring for 12 h, the product was purified using reverse-phase HPLC (MeCN/0.1% NH$_4$HCO$_3$ in water) and lyophilized to give a white solid (6.2 mg). MS (ESI(+)) m/z 696.4 (M+H)$^+$.

Example 3

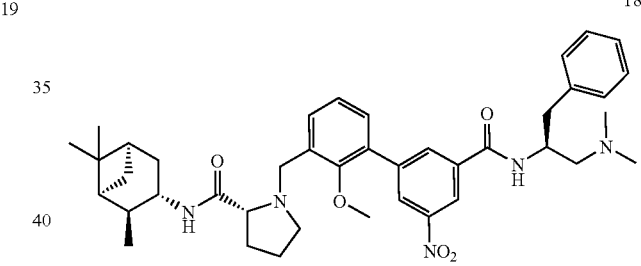

18

Compound 18 was synthesized according to the procedure described in Example 2, using Boc-D-proline in place of Boc-L-proline. MS (ESI(+)) m/z 696.4 (M+H)+.

Example 4

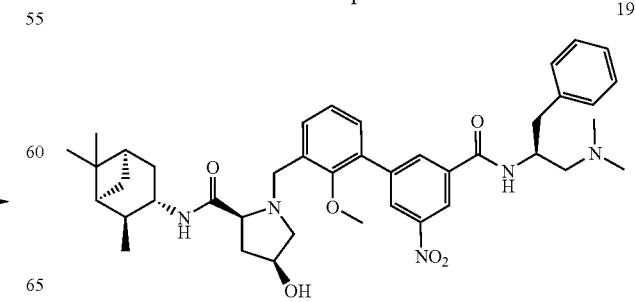

19

Compound 19 was synthesized according to the procedure described in Example 2, using hydroxy-Boc-L-proline in place of Boc-L-proline.
Example 5
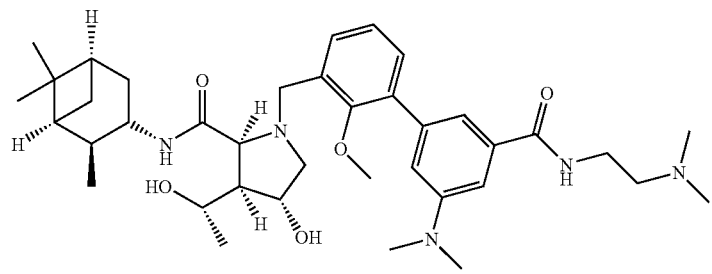
20
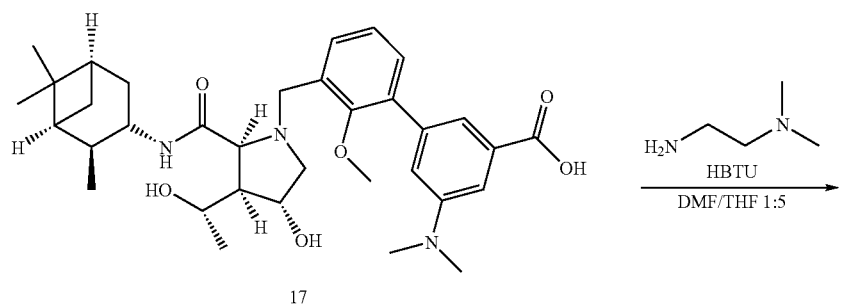
17
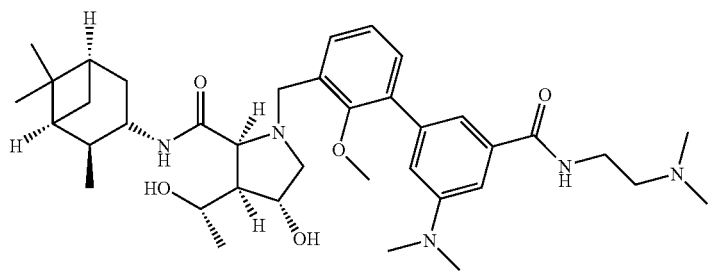
20
Compound 20 was synthesized according to the procedure described in Example 1, using N,N-dimethylamino ethyl amine in place of phenethylamine. 70% overall yield. Parent MS (ESI(+)) m/z 664.16 (M+H)+, Major ion fragment m/z 332.56 (M+2H/2)+
Example 6
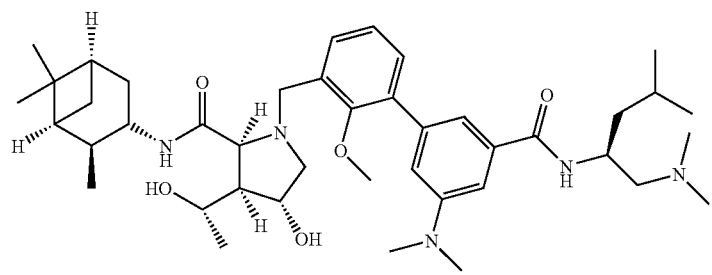
21

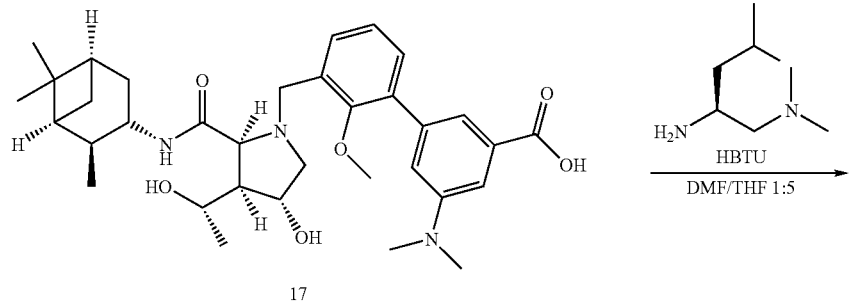
17
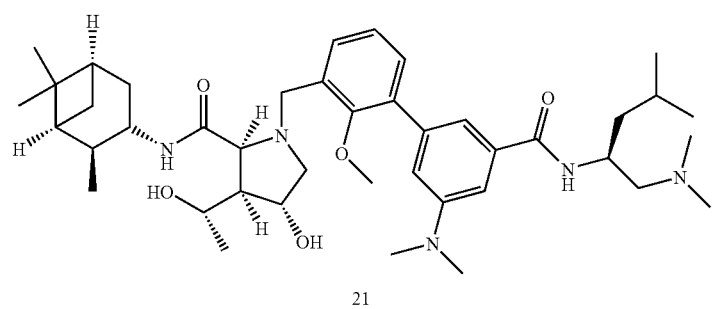
21
Compound 21 was synthesized according to the procedure described in Example 1, using (S)—N'N'-4-trimethylpentane-1,2-diamine in place of phenethylamine. 70% overall yield. Parent MS (ESI(+)) m/z 720.25 (M+H)+, major ion fragment m/z 360.52 (M+2H/2)+.
Example 7
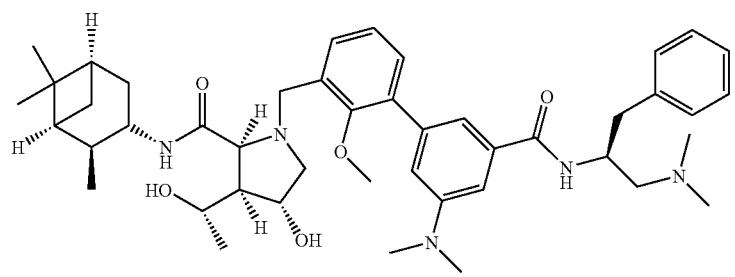
22
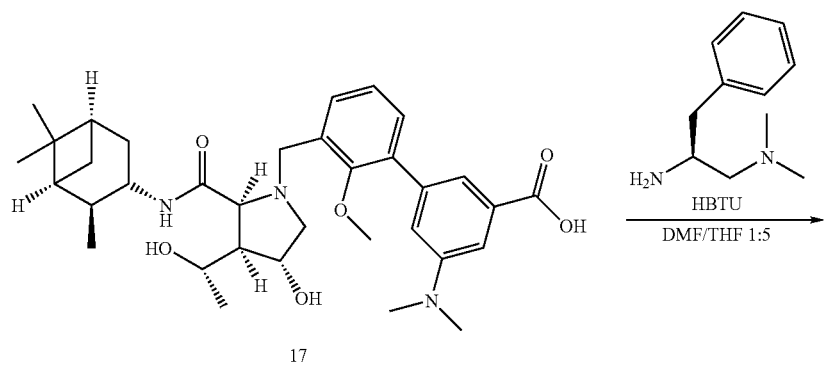
17

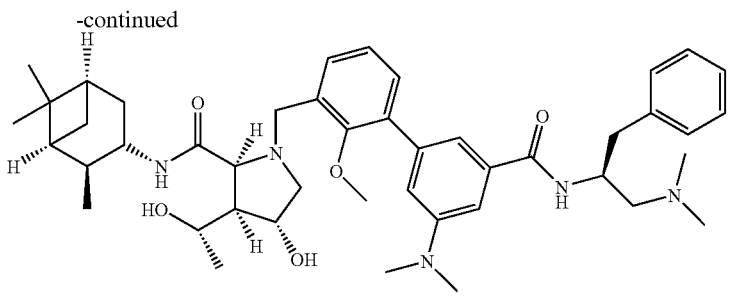
22
Compound 22 was synthesized according to the procedure described in Example 1, using (S)—N'N'-dimethyl-3-phenyl-propane-1,2-in place of phenethylamine. 70% overall yield. Parent MS (ESI(+)) m/z 754.23 (M+H)+, major ion fragment m/z 377.59 (M+2H/2).
Example 8
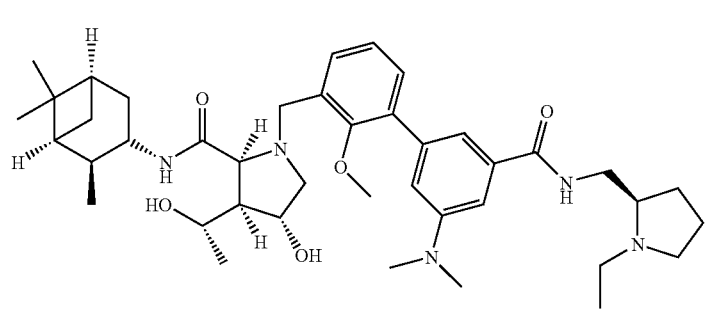
23
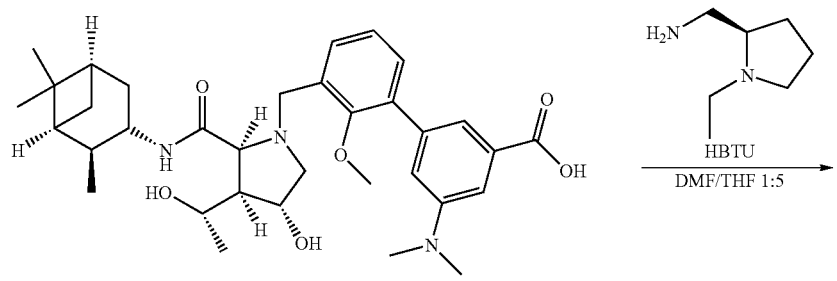
17
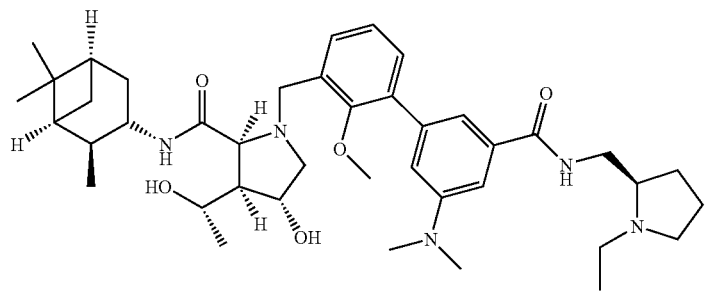
23

Compound 22 was synthesized according to the procedure described in Example 1, using 1-ethyl-(S)-2-Pyrrolidinemethanamine in place of phenethylamine. 70% overall yield. Parent MS (ESI(+)) m/z 704.3 (M+H)+, major ion fragment m/z 352.65 (M+2H/2).
Example 9
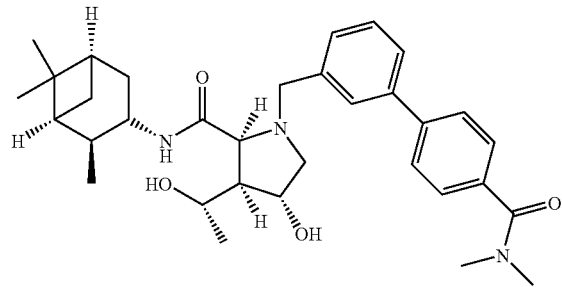
24
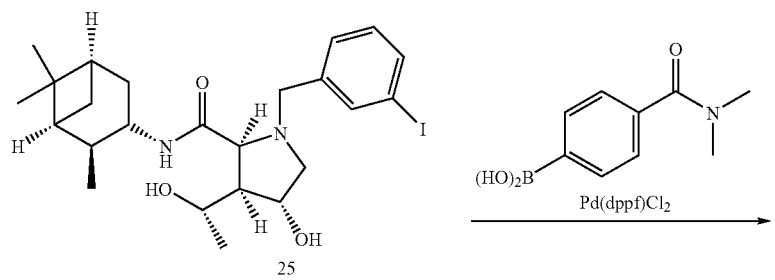
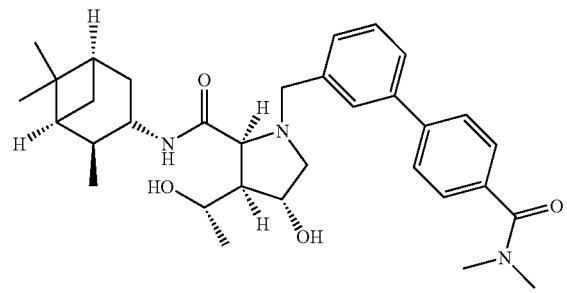
24

Under an argon atmosphere compound 25 (synthesized according to procedure described in Example 1, compound 12) (100 mg), 4-(dimethylaminocarbonyl)phenylboronic acid (71 mg), Cs₂CO₃ (120 mg), KOAc (20 mg), and Pd(dppf)Cl₂ (10 mg) were suspended in DMSO (6 mL) and heated at 60° C. during 3 h. Additional Pd(dppf)Cl₂ (5 mg) was added to the reaction mixture after 2.5 h. The reaction mixture was then cooled to rt and diluted with DCM (25 mL) and then extracted with aqueous solution of NaS₂CNMe₂ (8 mL). The aqueous layer was separated and extracted with DCM (3×25 mL). The combined organics were washed with water (25 mL) and brine (25 mL), dried on Na₂SO₄, and concentrated under reduced pressure. The crude material was purified using silica gel column chromatography to yield the desired product.

Example 10

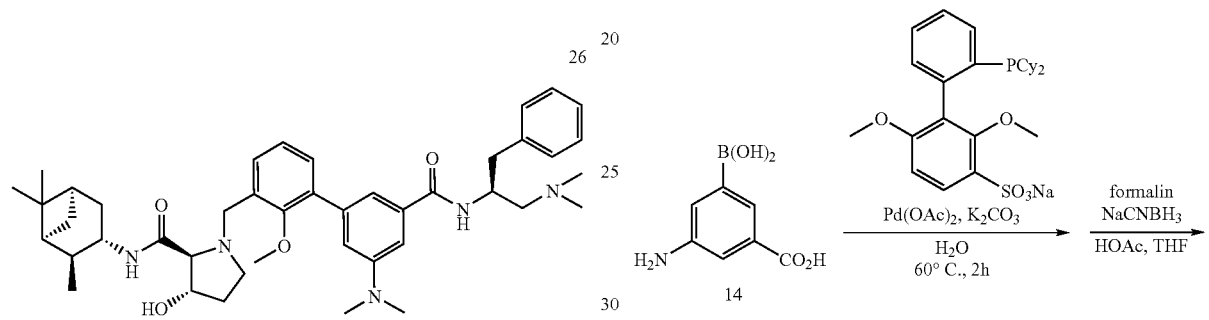

Part A

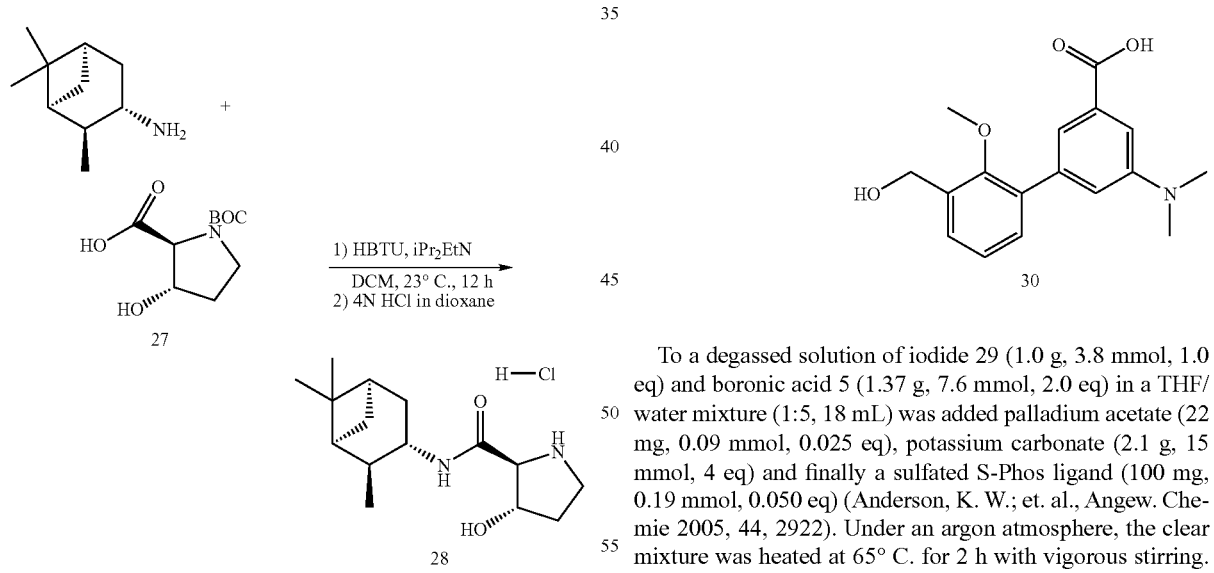

Boc-L-3-trans-hydroxyproline 27 (250 mg, 1.08 mmol, 1.0 eq) and (+)-isopinocamphylamine (166 mg, 1.08 mmol, 1.0 eq) with diisopropylethylamine (280 mg, 2.16 mmol, 2.0 eq) were dissolved in DCM (5 mL) and treated with HBTU (492.0 mg, 1.3 mmol, 1.2 eq). The mixture was stirred at rt for 12 h and then poured into diethylether (40 mL) and water (20 mL). The organic layer was washed sequentially with additional water (20 mL), 5% sodium bicarbonate, 1 M hydrochloric acid, saturated aqueous sodium chloride, and then dried over sodium sulfate. The oil produced from concentration was restored in diethylether (5 mL) and stirred with hydrochloric acid in dioxane (4 M, 5 mL) for 4 h. The solution was concentrated in vacuo and dried to produce 3 as a white solid. 80% yield.

Part B

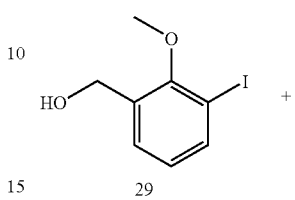

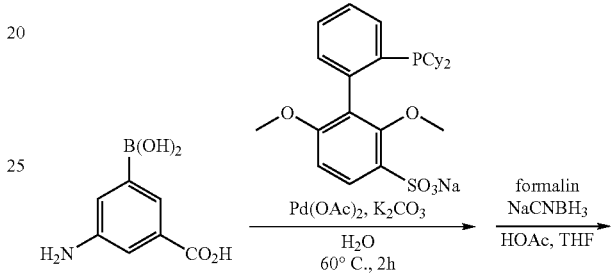

To a degassed solution of iodide 29 (1.0 g, 3.8 mmol, 1.0 eq) and boronic acid 5 (1.37 g, 7.6 mmol, 2.0 eq) in a THF/water mixture (1:5, 18 mL) was added palladium acetate (22 mg, 0.09 mmol, 0.025 eq), potassium carbonate (2.1 g, 15 mmol, 4 eq) and finally a sulfated S-Phos ligand (100 mg, 0.19 mmol, 0.050 eq) (Anderson, K. W.; et. al., Angew. Chemie 2005, 44, 2922). Under an argon atmosphere, the clear mixture was heated at 65° C. for 2 h with vigorous stirring. The reaction mixture was allowed to cool to rt and was then diluted with THF (3 mL) and acetic acid (3 mL). To this stirring mixture was added formalin solution (2.4 mL, 30 mmol, 8.0 eq) and sodium cyanoborohydride (710.0 mg, 11 mmol, 3.0 eq). After stirring for 15 min, the mixture was diluted with water (50 mL) and extracted twice with EtOAc (2×75 mL). The combined organic layers were washed with saturated aqueous sodium chloride (30 mL) and dried over sodium sulfate. Concentration in vacuo provided a pale yellow oil of 30 that was used in the subsequent reaction without further purification.

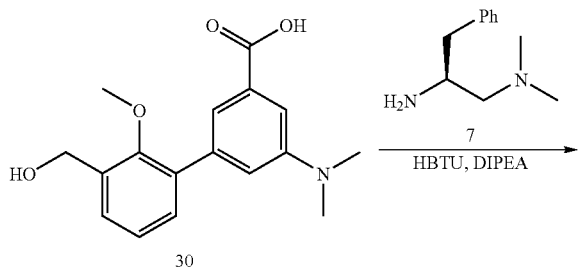
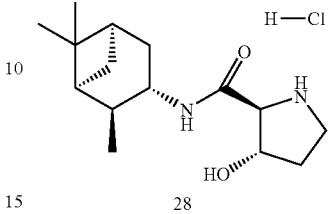

Part C

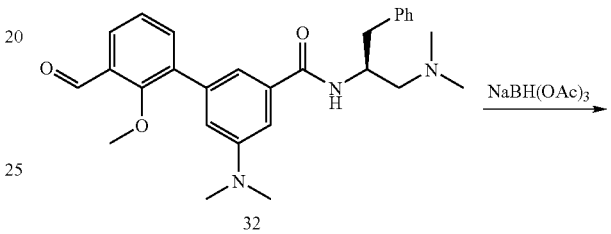

The yellow oil 30 from the previous step (3.8 mmol, 1.0 eq) with diamine 7 (810 mg, 4.5 mmol, 1.2 eq) and diisopropylethylamine (2.0 mL, 11 mmol, 3.0 eq) was dissolved in DCM (10 mL) and treated with HBTU (1.7 g, 4.5 mmol, 1.2 eq) and stirred at rt for 2 h. The clear solution was mixed with 5% aqueous sodium bicarbonate (50 mL) and extracted twice with DCM (2×50 mL). The combined organic extracts were washed with brine (25 mL), dried over sodium sulfate, and concentrated in vacuo. The crude mixture was purified by silica gel chromatography (0.5% ammonium hydroxide/3-10% methanol/DCM) to afford a white foam of 31 (610 mg, 35% for three steps). MS (ESI(+)) 462.4 m/z (M+H)$^+$.

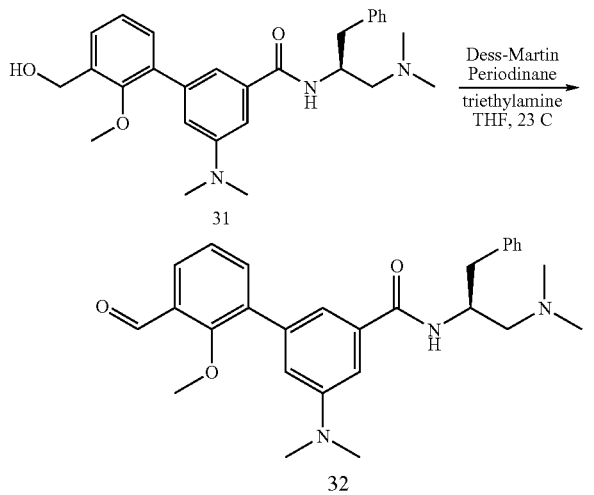

To a DCM solution (4 mL) of alcohol 31 (165 mg, 0.35 mmol, 1.0 eq) was added triethylamine (0.3 mL, 2.1 mmol, 6.0 eq) followed by Dess-Martin periodinane (212 mg, 0.5 mmol, 1.4 eq). The reaction was stirred for 1.5 h at rt and then diluted with DCM (30 mL). The organic mixture was washed sequentially with 5% aqueous sodium thiosulfate, 5% sodium bicarbonate, water, and brine (25 mL each) and dried over sodium sulfate. Concentration in vacuo produced a light amber oil of 32 used directly in the next step. MS (ESI(+)) 460.4 m/z (M+H)$^+$.

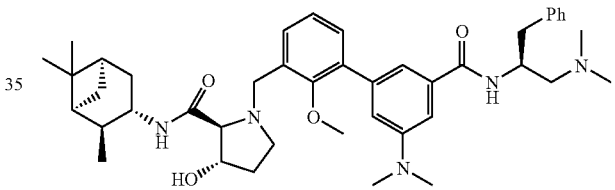

The amine hydrochloride 28 (60.0 mg, 0.2 mmol, 3.0 eq) and aldehyde 32 (30.0 mg, 0.065 mmol, 1.0 eq) were dissolved in methanol (1.2 mL) and treated with triethylamine (20.0 mg, 0.2 mL, 3.0 eq) and sodium triacetoxyborohydride (55.0 mg, 0.26 mmol, 4.0 eq). After stirring for 12 h, the product was purified using reverse-phase HPLC (MeCN/0.1% formic acid in water) and concentrated by lyophilization to give 26 as a white powder (4.0 mg). MS (ESI(+)) 710.7 m/z (M+H)$^+$.

Example 11

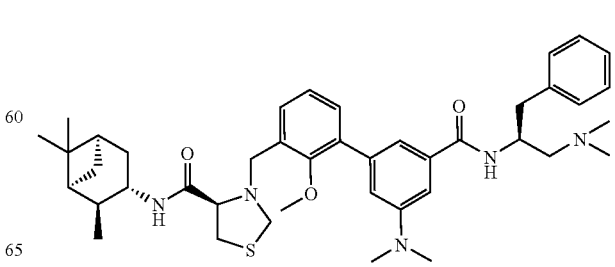

Compound 33 was synthesized according to the procedure described in Example 10, using Boc-L-4-thiaproline in place of Boc-L-3-trans-hydroxyproline. MS (ESI(+)) m/z 712.5 (M+H)+.

Example 12

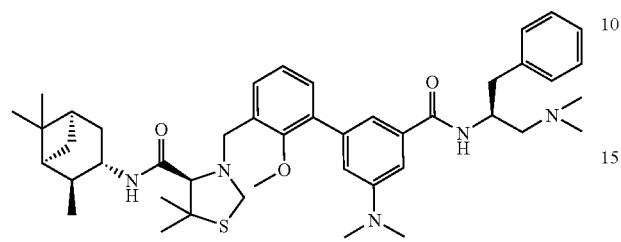

Compound 34 was synthesized according to the procedure described in Example 10, using Boc-L-3-dimethyl-4-thiaproline in place of Boc-L-3-trans-hydroxyproline. MS (ESI(+)) m/z 740.5 (M+H)+.

Example 13

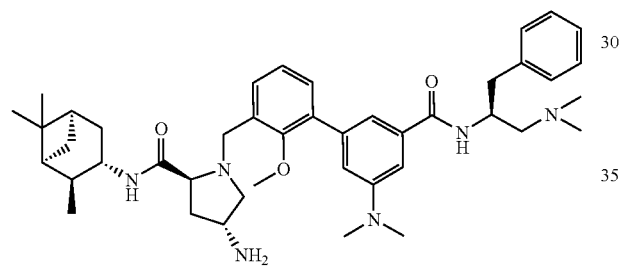

Compound 35 was synthesized according to the procedure described in Example 10, using Boc-L-4-trans-Fmoc-aminoproline in place of Boc-L-3-trans-hydroxyproline. Before final purification, the Fmoc group was removed by treatment with 15% piperdine in methanol. This methanol solution was submitted directly to reverse-phase HPLC. MS (ESI(+)) m/z 708.5 (M+H)+.

Example 14

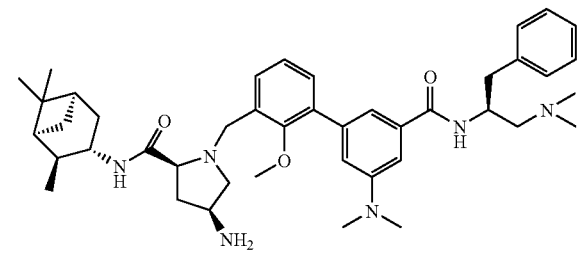

Compound 36 was synthesized according to the procedure described in Example 10, using Boc-L-4-cis-Fmoc-aminoproline in place of Boc-L-3-trans-hydroxyproline. Before final purification, the Fmoc group was removed by treatment with 15% piperdine in methanol. This methanol solution was submitted directly to reverse-phase HPLC. MS (ESI(+)) m/z 708.5 (M+H)+.

Example 15

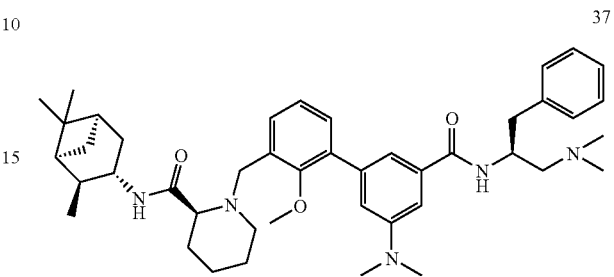

Compound 37 was synthesized according to the procedure described in Example 10, using Boc-L-pipecolic acid in place of Boc-L-3-trans-hydroxyproline. MS (ESI(+)) m/z 708.5 (M+H)+.

Example 16

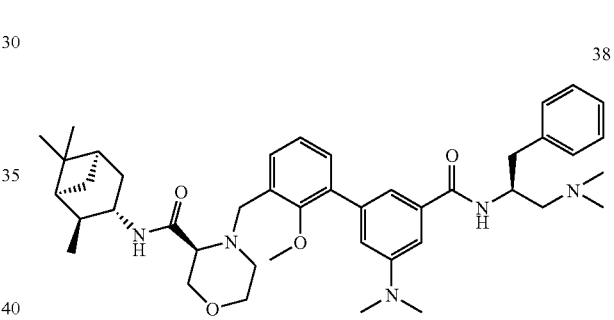

Compound 38 was synthesized according to the procedure described in Example 1, using Boc-S-2-morpholinecarboxylic acid in place of Boc-L-3-trans-hydroxyproline. MS (ESI (+)) m/z 710.5 (M+H)+.

Example 17

Bcl-2 binding affinity analysis data is presented below for various compounds of the invention. Note that "**" indicates that the Ki is <0.1 µM; "*" indicates that the Ki is 0.1-0.3 µM; "**" indicates that the Ki is 0.3-50 µM; and "*" indicates that the Ki is >50 µM.

| Compound | Bcl Ki |
|---|---|
| 1 | **** |
| 13 | * |
| 18 | ** |
| 23 | **** |
| 24 | * |
| 26 | **** |
| 33 | **** |
| 34 | **** |
| 35 | **** |
| 36 | **** |

-continued

| Compound | Bcl Ki |
|---|---|
| 37 | * |
| 38 | ** |

INCORPORATION BY REFERENCE

All of the U.S. patents, U.S. patent application publications, and PCT patent application publications designating the U.S. that are cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:
1. A compound represented by formula 1:

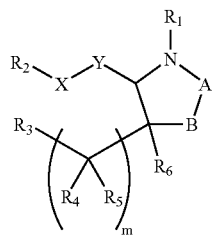

or an unsaturated form thereof or a pharmaceutically acceptable salt thereof;
wherein
Y is —C($R_{10}$)$_2$—, —(C=O)—, —(C=S)—, or —C(=N$R_{10}$)—;
X is —N($R_{10}$)—, or a bond;
m is 0, 1, 2, 3, 4, 5, or 6;
A is —C($A_1$)($A_2$)-;
each of $A_1$ and $A_2$ is independently H, alkyl, alkenyl, alkynyl, aryl, cycloalkyl, aralkyl, heterocyclyl, heteroaryl, heteroaralkyl, —C(O)N($R_{10}$)$_2$, —C(O)$R_{10}$, —CO$_2R_{10}$, —S(O)$_2$N($R_{10}$)$_2$, —S(O)$R_{10}$, —S(O)$_2$O$R_{10}$, —S(O)$_2$$R_{10}$; or has the formula 1a:

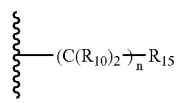

wherein independently for each occurrence of 1a;
n is 1, 2, 3, 4, 5, or 6;
$R_{15}$ is aryl, cycloalkyl, cycloalkenyl, heterocyclyl, heteroaryl, —O$R_{10}$, —S$R_{10}$, —N($R_{10}$)$_2$, —N($R_{10}$)CO$_2R_{10}$, —N($R_{10}$)C(O)N($R_{10}$)$_2$, —CO$_2R_{10}$, or —C(O)N($R_{10}$)$_2$; or is a polycyclic ring containing 8-14 carbon atoms, of which one, two or three ring atoms are independently S, O or N;

or $A_1$ and $A_2$ taken together form =O or =S; or $A_1$ and $A_2$ taken together with the carbon to which they are attached form a 5 to 8 membered heterocyclyl, of which one or two ring atoms are independently S, O or N;
B is S, or has the formula 1b:

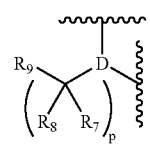

wherein
D is N or CR$_{10}$;
p is 0, 1, 2, 3, 4, or 5;
each of $R_7$ and $R_8$ is independently for each occurrence H, alkyl, alkenyl, alkynyl, aralkyl, aryl, cycloalkyl, heterocyclyl, cycloalkenyl, or heteroaryl; or $R_7$ and $R_8$ taken together form a 3-8 membered ring; or $R_7$ and $R_8$ taken together form a 4-8 membered ring;
$R_9$ is H, heterocyclyl, heteroaryl, —O$R_{10}$, —S$R_{10}$, —N($R_{10}$)$_2$, —N($R_{10}$)CO$_2R_{10}$, —N($R_{10}$)C(O)N($R_{10}$)$_2$, —CO$_2R_{10}$, —OCO$_2R_{10}$, —OC(O)N($R_{10}$)$_2$, —C(O)N($R_{10}$)$_2$, halide, nitrile, nitro, or acylthio;
$R_1$ has the formula 1c:

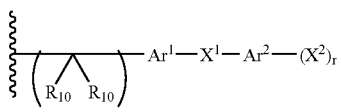

wherein
q is 0, 1, 2, 3, 4, or 5;
r is 0, 1, 2, 3, 4, or 5;
Ar$^1$ is represented by formula 1d:

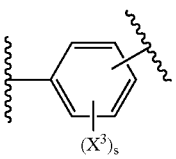

Wherein
s is 0, 1, 2, 3, or 4;
$X^2$ is independently for each occurrence H, alkyl, alkenyl, alkynyl, aryl, cycloalkyl, heterocyclyl, aralkyl, heteroaryl, heteroaralkyl, hydroxyl, acyloxy, nitrile, nitro, halide, O$R_{11}$, —C(O)N($R_{10}$)($R_{11}$), —C(O)$R_{11}$, —CO$_2R_{11}$, —S(O)$_2$N($R_{10}$)($R_{11}$), S$R_{11}$, —S(O)$R_{11}$, —S(O)$_2$O$R_{11}$, —S(O)$_2R_{11}$, —C(=N$R_{10}$)N($R_{10}$)($R_{11}$), or —C(=N$R_{10}$)($R_{11}$); or has the formula 1a;
$X^3$ is independently for each occurrence H, alkyl, alkynyl, aryl, cycloalkyl, heterocyclyl, aralkyl, heteroaryl, heteroaralkyl, hydroxyl, acyloxy, nitrile, nitro, halide, O$R_{11}$, —C(O)N($R_{10}$)($R_{11}$), —C(O)$R_{11}$, —S(O)$_2$N($R_{10}$)($R_{11}$), S$R_{11}$, —S(O)$R_{11}$, —S(O)$_2$O$R_{11}$, —S(O)$_2$ $R_{11}$, —C(=N$R_{10}$)N($R_{10}$)($R_{11}$), or —C(=N$R_{10}$)($R_{11}$); or has the formula 1a;
Ar$^2$ is a monocyclic or bicyclic aryl with 6-14 ring atoms; or a monocyclic or bicyclic heteroaryl with 5-14 ring atoms, of which one, two or three ring atoms are independently S, O or N;

$X^1$ is a bond, $-C(R_{10})_2-$, $-S-$, $-(NR_{10})-$, or $-O-$;

$R_2$ is H, a branched or unbranched alkyl or alkenyl, cycloalkyl, heterocyclyl, or bicycloalkyl; or has the formula 1a:

$R_3$ is H, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, $-OCO_2R_{10}$, $-OC(O)N(R_{10})_2$, $-C(O)N(R_{10})_2$, halide, nitrile, nitro, or acylthio;

each of $R_4$, $R_5$ and $R_{10}$ independently for each occurrence is H, alkyl, alkenyl, alkynyl, aralkyl, aryl, cycloalkyl, cycloalkenyl, bicycloalkyl, heterocyclyl, or heteroaryl; or has the formula 1a; or any two instances of $R_{10}$ taken together form a 3-8 membered ring; or $R_4$ and $R_5$ taken together form a 3-8 membered ring;

$R_6$ is H or alkyl;

$R_{11}$ is independently for each occurrence H, alkyl, alkenyl, alkynyl, aralkyl, aryl, cycloalkyl, cycloalkenyl, bicycloalkyl, heterocyclyl, heteroaryl, or $-[C(R_{12})(R_{13})]_t-R_{14}$;

wherein t is 0, 1, 2, 3, 4, or 5;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl.

2. The compound of claim 1, wherein the compound has the structure 2:

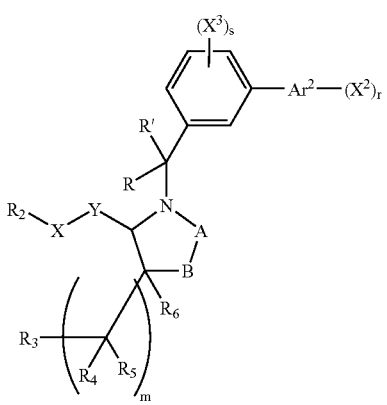

2 wherein

Y is $-C(R_{10})_2-$, $-(C=O)-$, or $-(C=S)-$;

X is $-N(R_{10})-$;

m is 0, 1, 2, or 3;

r is 0, 1, 2, 3, 4, or 5;

s is 0, 1, 2, 3, or 4;

A is $-C(A_1)(A_2)-$;

each of $A_1$ and $A_2$ is independently H, alkyl, aryl, cycloalkyl, aralkyl, heterocyclyl, heteroaryl, heteroaralkyl, $-C(O)N(R_{10})_2$, $-C(O)R_{10}$, $-CO_2R_{10}$, $-S(O)_2N(R_{10})_2$, $-S(O)R_{10}$, $-S(O)_2OR_{10}$, or $-S(O)_2R_{10}$; or has the formula 2a:

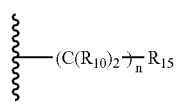

2a wherein independently for each occurrence of 2a;

n is 1, 2, 3, 4, 5, or 6;

$R_{15}$ is aryl, cycloalkyl, cycloalkenyl, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, or $-C(O)N(R_{10})_2$; or is a polycyclic ring containing 8-14 carbon atoms, of which one, two or three ring atoms are independently S, O or N;

or $A_1$ and $A_2$ taken together form $=O$ or $=S$;

B is S or has the formula 2b:

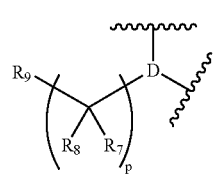

2b wherein

D is N or $CR_{10}$;

p is 0, 1, 2, or 3;

each of $R_7$ and $R_8$ is independently for each occurrence H, alkyl, alkenyl, alkynyl, aralkyl, aryl, cycloalkyl, heterocyclyl, cycloalkenyl, or heteroaryl; or $R_7$ and $R_8$ taken together form a 3-8 membered ring; or $R_7$ and $R_8$ taken together form a 4-8 membered ring;

$R_9$ is H, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, $-OCO_2R_{10}$, $-OC(O)N(R_{10})_2$, $-C(O)N(R_{10})_2$, halide, nitrile, nitro, or acylthio;

$Ar^2$ is a monocyclic or bicyclic aryl with 6-10 ring atoms; or a monocyclic or bicyclic heteroaryl with 5-14 ring atoms, of which one, two or three ring atoms are independently S, O or N;

$X^2$ is independently for each occurrence H, alkyl, alkenyl, alkynyl, aryl, cycloalkyl, heterocyclyl, aralkyl, heteroaryl, heteroaralkyl, hydroxyl, acyloxy, nitrile, nitro, halide, $OR_{11}$, $-C(O)N(R_{10})(R_{11})$, $-C(O)R_{11}$, $-CO_2R_{11}$, $-S(O)_2N(R_{10})(R_{11})$, $SR_{11}$, $-S(O)R_{11}$, $-S(O)_2OR_{11}$, $-S(O)_2R_{11}$, $-C(=NR_{10})N(R_{10})(R_{11})$, or $-C(=NR_{10})(R_{11})$; or has the formula 2a;

each of $R_4$, $R_5$ and $R_{10}$ is independently for each occurrence H, alkyl, alkenyl, alkynyl, aralkyl, aryl, cycloalkyl, cycloalkenyl, bicycloalkyl, heterocyclyl, or heteroaryl; or has the formula 2a; or any two instances of $R_{10}$ taken together form a 3-8 membered ring; or $R_4$ and $R_5$ taken together form a 3-8 membered ring;

$X^3$ is independently for each occurrence H, alkyl, $-OR_{11}$, or halide; or has formula 2a;

each of R and R' is independently for each occurrence H or alkyl;

$R_6$ is H or alkyl;

$R_{11}$ is independently for each occurrence H, alkyl, alkenyl, alkynyl, aralkyl, aryl, cycloalkyl, cycloalkenyl, bicycloalkyl, heterocyclyl, heteroaryl, or —[C($R_{12}$)($R_{13}$)]$_t$—$R_{14}$;

wherein t is independently for each occurrence 0, 1, 2, 3, 4, or 5;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl.

3. The compound of claim 2, wherein $Ar^2(X^2)_r$ is represented by the formula 3:

wherein $R_{18}$ is alkyl, alkenyl, halide, nitro, or amino;

each of $R_{20}$ and $R_{21}$ is independently H, alkyl, aralkyl, heteroaralkyl, alkoxy, or —[C($R_{22}$)($R_{23}$)]$_t$—$R_{24}$;

t is independently for each occurrence 0, 1, 2, 3, 4, or 5;

each of $R_{22}$ and $R_{23}$ is independently for each occurrence H, alkyl, aryl, aralkyl, cycloalkyl, heterocyclyl, heterocyclylalkyl, heteroaryl, or heteroaralkyl; and $R_{24}$ is independently for each occurrence H, alkyl, aryl, heteroaryl, heterocyclylalkyl, alkoxy, amino, amido, or carboxyl.

4. The compound of claim 1, wherein the compound has the formula 4 wherein

Y is —C($R_{10}$)$_2$—, —(C=O)—, or —(C=S)—;

X is —N($R_{10}$)—;

m is 0, 1, 2, 3, or 4;

s is 0, 1, 2, 3;

each of $A_1$ and $A_2$ is independently H, alkyl, aryl, cycloalkyl, aralkyl, heterocyclyl, heteroaryl, heteroaralkyl, —C(O)N($R_{10}$)$_2$, —C(O)$R_{10}$, —CO$_2R_{10}$, —S(O)$_2$N($R_{10}$)$_2$, —S(O)$R_{10}$, —S(O)$_2R_{10}$, —S(O)$_2$OR$_{10}$, or —S(O)$_2$ $R_{10}$; or has the formula 4a:

wherein independently for each occurrence of 4a;

n is 1, 2, 3, 4, 5, or 6; and $R_{15}$ is aryl, cycloalkyl, cycloalkenyl, heterocyclyl, heteroaryl, —OR$_{10}$, —SR$_{10}$, —N($R_{10}$)$_2$, —N($R_{10}$)CO$_2R_{10}$, —N($R_{10}$)C(O)N($R_{10}$)$_2$, —CO$_2R_{10}$, or —C(O)N($R_{10}$)$_2$; or is a polycyclic ring containing 8-14 carbon atoms, of which one, two or three ring atoms are independently S, O or N;

or $A_1$ and $A_2$ taken together form =O or =S;

B is S or has the formula 4b:

wherein

D is N or CR$_{10}$;

p is 0, 1, 2, 3;

each of $R_7$ and $R_8$ is independently for each occurrence H, alkyl, alkenyl, alkynyl, aralkyl, aryl, cycloalkyl, heterocyclyl, cycloalkenyl, or heteroaryl; or $R_7$ and $R_8$ taken together form a 3-8 membered ring; or $R_7$ and $R_8$ taken together form a 4-8 membered ring;

$R_9$ is H, heterocyclyl, heteroaryl, —OR$_{10}$, —SR$_{10}$, —N($R_{10}$)$_2$, —N($R_{10}$)CO$_2R_{10}$, —N($R_{10}$)C(O)N($R_{10}$)$_2$, —CO$_2R_{10}$, —OCO$_2R_{10}$, —OC(O)N($R_{10}$)$_2$, —C(O)N($R_{10}$)$_2$, halide, nitrile, nitro, or acylthio;

$R_6$ is H or alkyl;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl;

$R_{14}$ is independently for each occurrence H, alkyl, aryl, heteroaryl, heterocyclylalkyl, alkoxy, amino, amido, or carboxyl;

$R_{16}$ is H, alkyl, alkenyl, or OR$_{11}$; has the formula 4a;

each of $X^3$ independently for each occurrence is H or halide;

$R_{18}$ is alkyl, alkenyl, halide, nitro, or amino;

each of $R_{20}$ and $R_{21}$ is independently H, alkyl, aralkyl, heteroaralkyl, alkoxy, or —[C($R_{22}$)($R_{23}$)]$_t$—$R_{24}$;

t is independently for each occurrence 1, 2, 3, 4, or 5;

each of $R_{22}$ and $R_{23}$ is independently for each occurrence H, alkyl, aryl, aralkyl, cycloalkyl, heterocyclyl, heterocyclylalkyl, heteroaryl, or heteroaralkyl; and $R_{24}$ is independently for each occurrence H, alkyl, aryl, heteroaryl, heterocyclylalkyl, alkoxy, amino, amido, or carboxyl.

5. The compound of claim 4, wherein Y is —(C=O)— and X is —NH—.

6. The compound of claim 4, wherein B has the formula 6a or 6b:

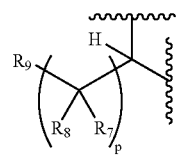

6a

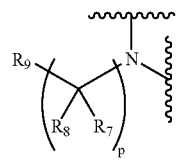

6b wherein
p is 0, 1, or 2;
each of $R_7$ and $R_8$ independently for each occurrence is H or alkyl; and
$R_9$ is H, —$OR_{10}$, —$N(R_{10})_2$, —$N(R_{10})CO_2R_{10}$, —$N(R_{10})C(O)N(R_{10})_2$, —$OCO_2R_{10}$, or —$OC(O)N(R_{10})_2$.

7. The compound of claim 4, wherein B is S.

8. The compound of claim 4, wherein $A_1$ and $A_2$ taken together form =O and B has the formula 8:

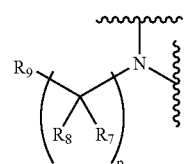

8 wherein
p is 0, 1 or 2;
each of $R_7$ and $R_8$ independently for each occurrence is H or alkyl; and
$R_9$ is H, —$OR_{10}$, —$N(R_{10})_2$, —$N(R_{10})CO_2R_{10}$, —$N(R_{10})C(O)N(R_{10})_2$, —$OCO_2R_{10}$, or —$OC(O)N(R_{10})_2$.

9. The compound of claim 8, wherein $A_1$ and $A_2$ are each H.

10. A compound represented by formula 10:

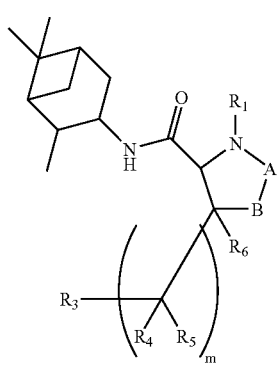

10 or an unsaturated form thereof or a pharmaceutically acceptable salt thereof;

wherein m represents independently for each occurrence 0, 1, 2, 3, 4, 5, or 6;

A is —$C(A_1)(A_2)$-;

each of $A_1$ and $A_2$ is independently H, alkyl, alkenyl, alkynyl, aryl, cycloalkyl, aralkyl, heterocyclyl, heteroaryl, heteroaralkyl, —$C(O)N(R_{10})_2$, —$C(O)R_{10}$, —$CO_2R_{10}$, —$S(O)_2N(R_{10})_2$, —$S(O)R_{10}$, —$S(O)_2OR_{10}$, or —$S(O)_2R_{10}$; or has the formula 10a:

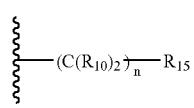

10a wherein independently for each occurrence of 10a;

n is 1, 2, 3, 4, 5, or 6; and $R_{15}$ is aryl, cycloalkyl, cycloalkenyl, heterocyclyl, heteroaryl, —$OR_{10}$, —$SR_{10}$, —$N(R_{10})_2$, —$N(R_{10})CO_2R_{10}$, —$N(R_{10})C(O)N(R_{10})_2$, —$CO_2R_{10}$, or —$C(O)N(R_{10})_2$; or is a polycyclic ring containing 8-14 carbon atoms, of which one, two or three ring atoms are independently S, O or N;

or $A_1$ and $A_2$ taken together form =O or =S; or $A_1$ and $A_2$ taken together with the carbon to which they are attached form a 5 to 8 heterocyclyl, of which one or two ring atoms are independently S, O or N B is S or has the formula 10b:

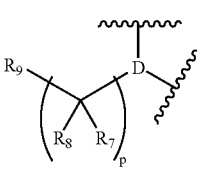

10b wherein
D is N or $CR_{10}$;
p is 0, 1, 2, 3, 4, or 5;
each of $R_7$ and $R_8$ is independently for each occurrence H, alkyl, alkenyl, alkynyl, aralkyl, aryl, cycloalkyl, heterocyclyl, cycloalkenyl, or heteroaryl; or $R_7$ and $R_8$ taken together form a 3-8 membered ring; or $R_7$ and $R_8$ taken together form a 4-8 membered ring;

$R_9$ is H, heterocyclyl, heteroaryl, —$OR_{10}$, —$SR_{10}$, —$N(R_{10})_2$, —$N(R_{10})CO_2R_{10}$, —$N(R_{10})C(O)N(R_{10})_2$, —$CO_2R_{10}$, —$OCO_2R_{10}$, —$OC(O)N(R_{10})_2$, —$C(O)N(R_{10})_2$, halide, nitrile, nitro, or acylthio;

$R_1$ has the formula 10c or 10d:

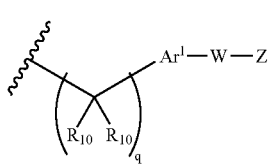

10c

-continued

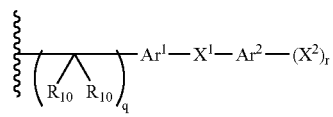

10d wherein q is 0, 1, 2, 3, 4, or 5;

r is 0, 1, 2, 3, 4, or 5;

W is a bond; or alkyl diradical, alkenyl diradical, or alkynyl diradical;

Z is H, $-SR_{10}$, $-S(O)_2R_{11}$, $-NR_{10}S(O)_2R_{11}$, $-S(O)R_{10}$, $-N(R_{10})(R_{11})$, $-C(O)R_{11}$, $-CO_2R_{11}$, $-C(O)N(R_{10})(R_{11})$, $-C(S)N(R_{10})(R_{11})$, $-CH_2C(O)$heterocyclyl, $-NR_{10}C(O)R_{11}$, $-NR_{10}CO_2R_{11}$, $-OC(O)N(R_{10})(R_{11})$, $-NC(O)CH(R_{10})(R_{11})$, $-C(=NR_{10})N(R_{10})(R_{11})$, $-C(=NR_{10})R_{11}$, hydroxyalkyl, monocyclic aryl, bicyclic aryl, heteroaryl, or heterocyclyl;

$Ar^1$ is represented by formula 10e:

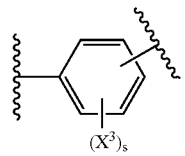

10e

Wherein s is 0, 1, 2, 3, or 4;

each of $X^2$ and $X^3$ is independently for each occurrence H, alkyl, alkenyl, alkynyl, aryl, cycloalkyl, heterocyclyl, aralkyl, heteroaryl, heteroaralkyl, hydroxyl, acyloxy, nitrile, nitro, halide, $OR_{11}$, $-C(O)N(R_{10})(R_{11})$, $-C(O)R_{11}$, $-CO_2R_{11}$, $-S(O)_2N(R_{10})(R_{11})$, $SR_{11}$, $-S(O)R_{11}$, $-S(O)_2OR_{11}$, $-S(O)_2R_{11}$, $-C(=NR_{10})N(R_{10})(R_{11})$, or $-C(=NR_{10})(R_{11})$; or has the formula 10a;

$Ar^2$ represent independently for each occurrence are monocyclic or bicyclic aryl with 6-14 ring atoms; or a monocyclic or bicyclic heteroaryl with 5-14 ring atoms, of which one, two or three ring atoms are independently S, O or N;

$X^1$ is a bond, $-C(R_{10})_2-$, $-S-$, $-N(R_{10})-$ or $-O-$;

$R_2$ is H, a branched or unbranched alkyl or alkenyl, cycloalkyl, heterocyclyl, or bicycloalkyl; or has the formula 10a:

$R_3$ is H, heterocyclyl, heteroaryl, $-OR_{10}$, $-SR_{10}$, $-N(R_{10})_2$, $-N(R_{10})CO_2R_{10}$, $-N(R_{10})C(O)N(R_{10})_2$, $-CO_2R_{10}$, $-OCO_2R_{10}$, $-OC(O)N(R_{10})_2$, $-C(O)N(R_{10})_2$, halide, nitrile, nitro, or acylthio;

each of $R_4$, $R_5$ and $R_{10}$ is independently for each occurrence H, alkyl, alkenyl, alkynyl, aralkyl, aryl, cycloalkyl, cycloalkenyl, bicycloalkyl, heterocyclyl, or heteroaryl; or has the formula 10a;

or any two instances of $R_{10}$ taken together form a 3-8 membered ring; or $R_4$ and $R_5$ taken together form a 3-8 membered ring;

$R_6$ is H or alkyl;

$R_{11}$ is independently for each occurrence H, alkyl, alkenyl, alkynyl, aralkyl, aryl, cycloalkyl, cycloalkenyl, bicycloalkyl, heterocyclyl, heteroaryl, or $-[C(R_{12})(R_{13})]_t-R_{14}$;

wherein t is 0, 1, 2, 3, 4, or 5;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl.

11. The compound of claim 10, wherein $R_1$ has the formula 11:

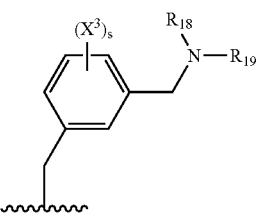

11 wherein s is 0, 1, 2, 3, or 4;

each of $X^3$ is independently for each occurrence H or halide;

each of $R_{18}$ and $R_{19}$ is independently H, alkyl, alkenyl, alkynyl, aralkyl, aryl, cycloalkyl, cycloalkenyl, bicycloalkyl, heterocyclyl, heteroaryl, or $-[C(R_{12})(R_{13})]_t-R_{14}$;

wherein t is 0, 1, 2, 3, 4, or 5;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl.

12. The compound of claim 10, wherein B has the formula 12a or 12b:

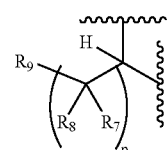

12a

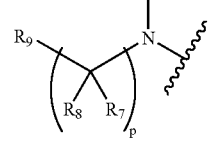

12b wherein p is 0, 1, 2, 3, or 4;

each of $R_7$ and $R_8$ is independently for each occurrence H or alkyl; and $R_9$ is H, —$OR_{10}$, —$N(R_{10})_2$, —$N(R_{10})CO_2R_{10}$, —$N(R_{10})C(O)N(R_{10})_2$, —$OCO_2R_{10}$, or —$OC(O)N(R_{10})_2$.

13. The compound of claim 10, wherein A is —$C(A_1)(A_2)$-; $A_1$ and $A_2$ taken together form =O and B has the formula 13:

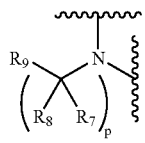

wherein
p is 0, 1, 2, 3, or 4;
each of $R_7$ and $R_8$ independently for each occurrence is H or alkyl; and
$R_9$ is H, —$OR_{10}$, —$N(R_{10})_2$, —$N(R_{10})CO_2R_{10}$, —$N(R_{10})C(O)N(R_{10})_2$, —$OCO_2R_{10}$, or —$OC(O)N(R_{10})_2$.

14. A compound represented by formula 14:

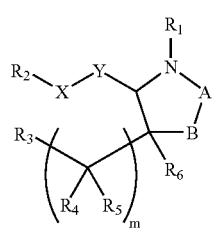

or an unsaturated form thereof or a pharmaceutically acceptable salt thereof;
wherein
Y is —$C(R_{10})_2$—, —(C=O)—, —(C=S)—, or —$C(=NR_{10})$—;
X is —$N(R_{10})$—, or a bond;
m represents independently for each occurrence 0, 1, 2, 3, 4, 5, or 6;
A is —$C(A_1)(A_2)$-;
each of $A_1$ and $A_2$ is independently for each occurrence H, alkyl, alkenyl, alkynyl, aryl, cycloalkyl, aralkyl, heterocyclyl, heteroaryl, heteroaralkyl, —$C(O)N(R_{10})_2$, —$C(O)R_{10}$, —$CO_2R_{10}$, —$S(O)_2N(R_{10})_2$, —$S(O)R_{10}$, —$S(O)_2OR_{10}$, —$S(O)_2R_{10}$; or has the formula 14a:

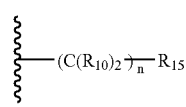

wherein independently for each occurrence of 14a;
n is 1, 2, 3, 4, 5, or 6; and
$R_{15}$ is aryl, cycloalkyl, cycloalkenyl, heterocyclyl, heteroaryl, —$OR_{10}$, —$SR_{10}$, —$N(R_{10})_2$, —$N(R_{10})CO_2R_{10}$, —$N(R_{10})C(O)N(R_{10})_2$, —$CO_2R_{10}$, or —$C(O)N(R_{10})_2$; or is a polycyclic ring containing 8-14 carbon atoms, of which one, two or three ring atoms are independently S, O or N;
or $A_1$ and $A_2$ taken together form =O or =S; or $A_1$ and $A_2$ taken together with the carbon to which they are attached form a 5 to 8 heterocyclyl, of which one or two ring atoms are independently S, O or N;

B is —$(C(R)_2X)$—, —$(XC(R)_2)$—, or —$(C(R_2)_2)$—;
X independently for each occurrence is S or —$(NR_{10})$—;
R independently for each occurrence is H, alkyl, alkenyl, alkynyl, aryl, cycloalkyl, aralkyl, heterocyclyl, heteroaryl, or heteroaralkyl; or has formula 14a;
$R_1$ has the formula 14b:

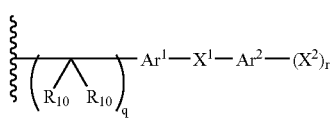

wherein
q is 0, 1, 2, 3, 4, or 5;
r is 0, 1, 2, 3, 4, or 5;
$Ar^1$ is represented by formula 14c:

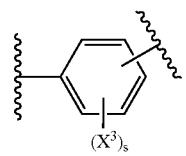

Wherein
s is 0, 1, 2, 3, or 4;
$X^2$ is independently for each occurrence H, alkyl, alkenyl, alkynyl, aryl, cycloalkyl, heterocyclyl, aralkyl, heteroaryl, heteroaralkyl, hydroxyl, acyloxy, nitrile, nitro, halide, —$OR_{11}$, —$C(O)N(R_{10})(R_{11})$, —$C(O)R_{11}$, —$CO_2R_{11}$, —$S(O)_2N(R_{10})(R_{11})$, —$SR_{11}$, —$S(O)R_{11}$, —$S(O)_2OR_{11}$, —$S(O)_2R_{11}$, —$C(=NR_{10})N(R_{10})(R_{11})$, or —$C(=NR_{10})(R_{11})$; or has the formula 14a;
$X^3$ is independently for each occurrence H, alkyl, alkynyl, aryl, cycloalkyl, heterocyclyl, aralkyl, heteroaryl, heteroaralkyl, hydroxyl, acyloxy, nitrile, nitro, halide, —$OR_{11}$, —$C(O)N(R_{10})(R_{11})$, —$C(O)R_{11}$, —$S(O)_2N(R_{10})(R_{11})$, —$SR_{11}$, —$S(O)R_{11}$, —$S(O)_2OR_{11}$, —$S(O)_2R_{11}$, —$C(=NR_{10})N(R_{10})(R_{11})$, or —$C(=NR_{10})(R_{11})$; or has the formula 14a;
$Ar^2$ represent independently for each occurrence are monocyclic or bicyclic aryl with 6-14 ring atoms; or a monocyclic or bicyclic heteroaryl with 5-14 ring atoms, of which one, two or three ring atoms are independently S, O or N;
$X^1$ is a bond, —$(C(R_{10})_2)$—, —S—, —$(NR_{10})$—, or —O—;
$R_2$ is H, a branched or unbranched alkyl or alkenyl, cycloalkyl, heterocyclyl, or bicycloalkyl; or has the formula 14a:
$R_3$ is H, heterocyclyl, heteroaryl, —$OR_{10}$, —$SR_{10}$, —$N(R_{10})_2$, —$N(R_{10})CO_2R_{10}$, —$N(R_{10})C(O)N(R_{10})_2$, —$CO_2R_{10}$, —$OCO_2R_{10}$, —$OC(O)N(R_{10})_2$, —$C(O)N(R_{10})_2$, halide, nitrile, nitro, or acylthio;
each of $R_4$, $R_5$ and $R_{10}$ is independently for each occurrence H, alkyl, alkenyl, alkynyl, aralkyl, aryl, cycloalkyl, cycloalkenyl, bicycloalkyl, heterocyclyl, or heteroaryl; or has the formula 14a;
or any two instances of $R_{10}$ taken together form a 3-8 membered ring; or $R_4$ and $R_5$ taken together form a 3-8 membered ring;

$R_6$ is H or alkyl;

$R_{11}$ independently for each occurrence is H, alkyl, alkenyl, alkynyl, aralkyl, aryl, cycloalkyl, cycloalkenyl, bicycloalkyl, heterocyclyl, heteroaryl, or —[C($R_{12}$)($R_{13}$)]$_t$—$R_{14}$;

wherein t is 0, 1, 2, 3, 4, or 5;

each of $R_{12}$ and $R_{13}$ is independently for each occurrence H, alkyl, aryl, aralkyl, cycloalkyl, heterocyclyl, heterocyclylalkyl, heteroaryl, or heteroaralkyl; and $R_{14}$ is independently for each occurrence H, alkyl, aryl, heteroaryl, heterocyclylalkyl, alkoxy, amino, amido, or carboxyl.

15. The compound of claim 14, wherein the compound has the formula 15:

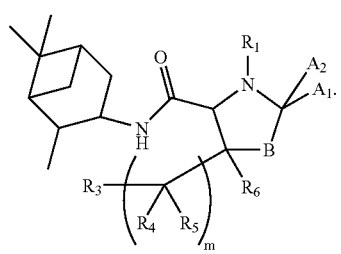

16. The compound of claim 14, wherein the compound has the formula 16:

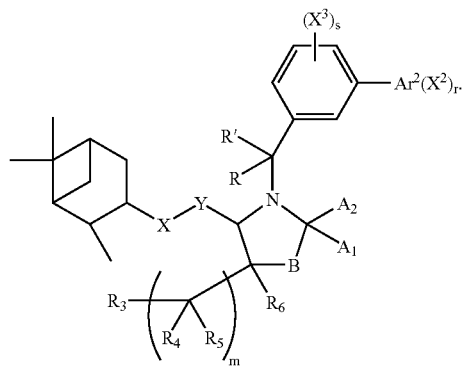

17. A compound selected from the group consisting of:

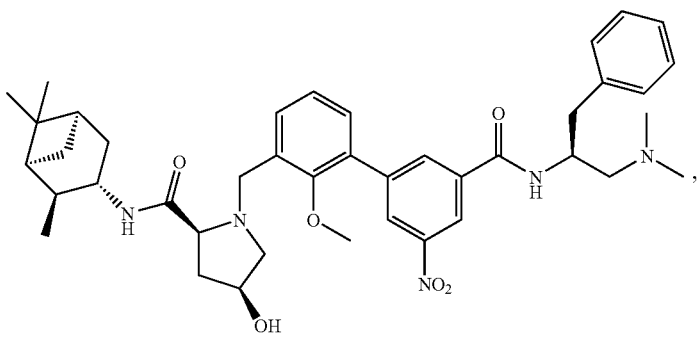

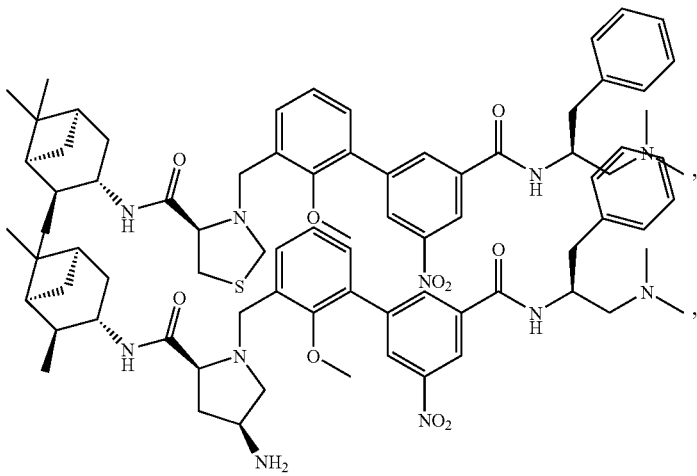

-continued
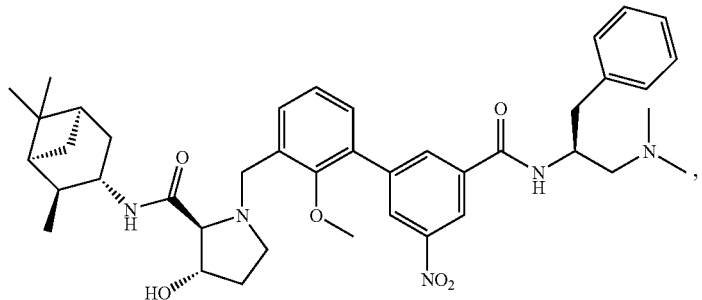
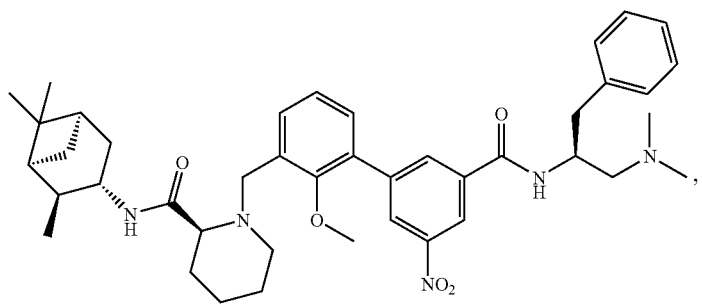
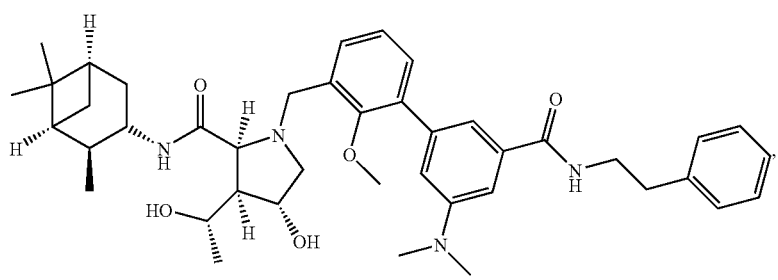
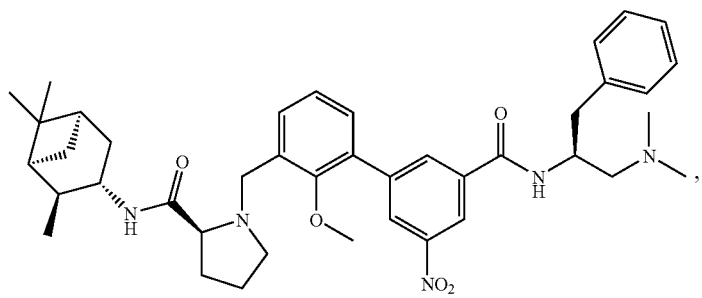
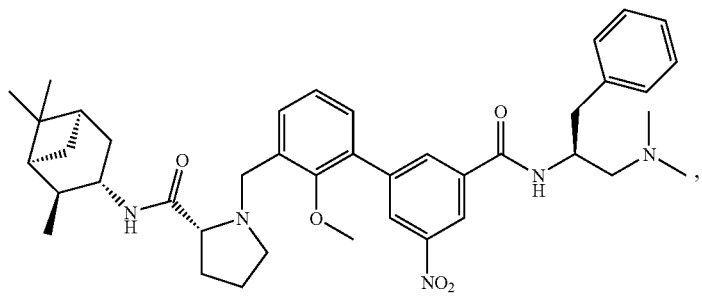

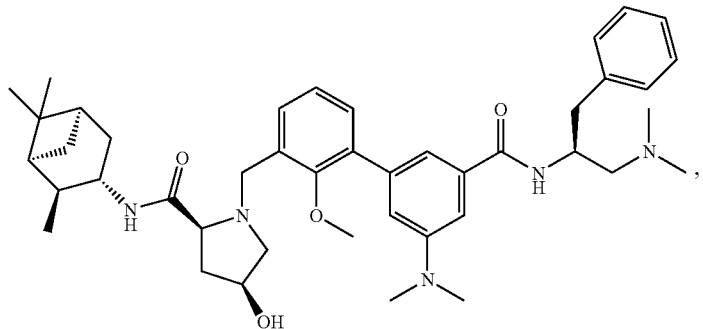
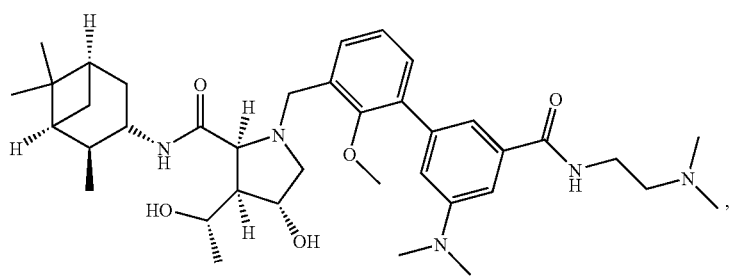
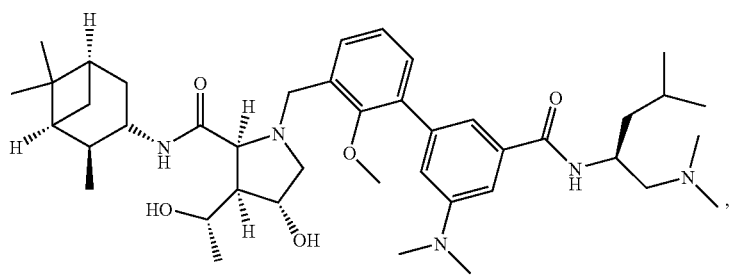
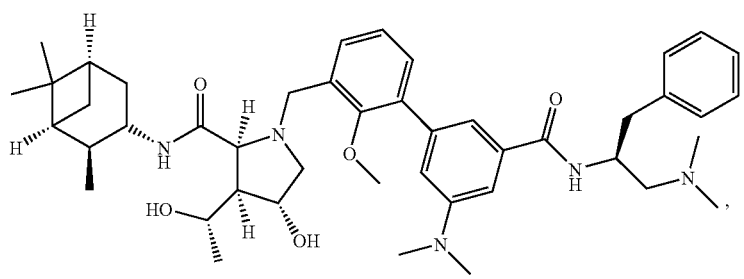
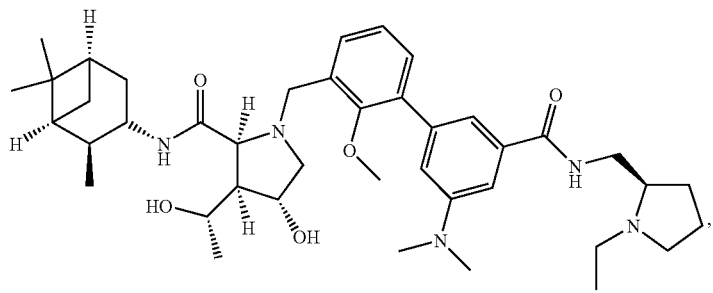

-continued
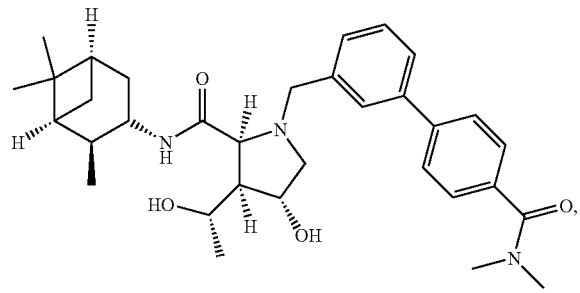
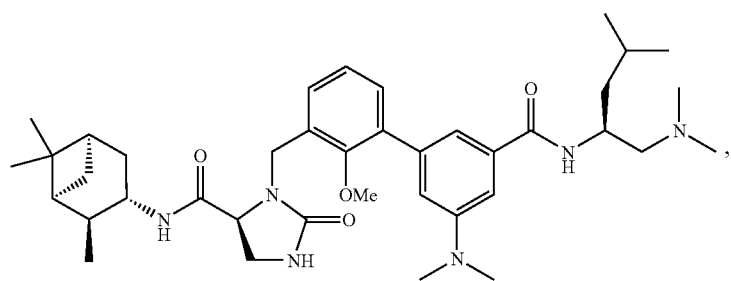
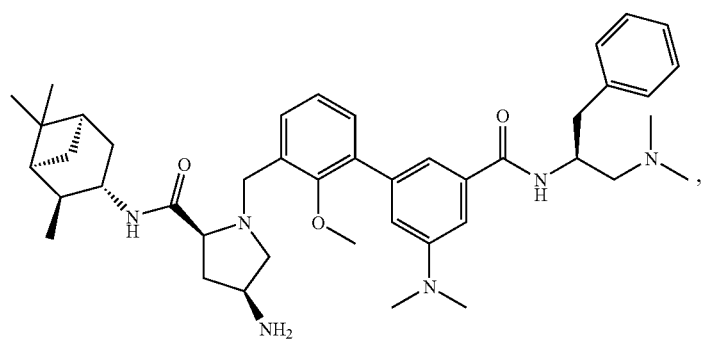
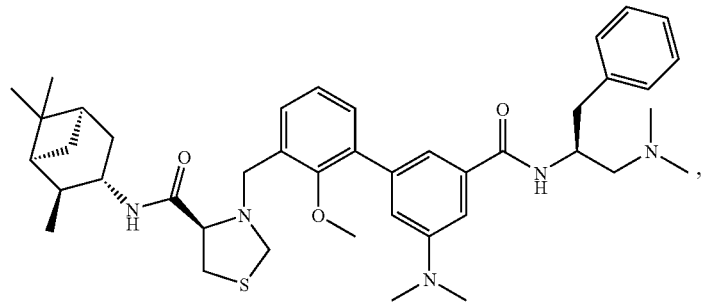
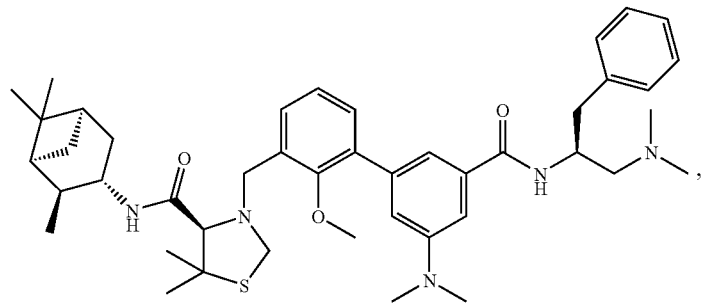

-continued
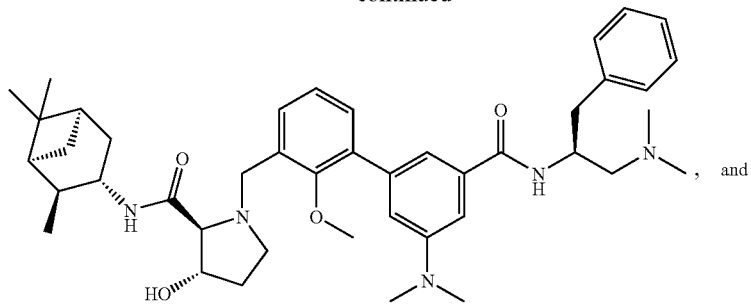, and
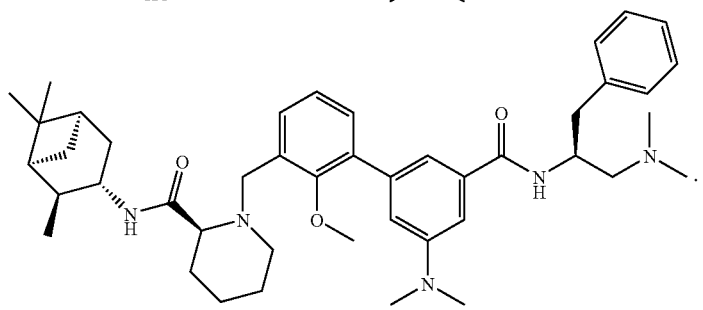.
18. A pharmaceutical composition, comprising a compound of claim 1, 10, 14, or 17; and at least one pharmaceutically acceptable excipient.
* * * * *